(12) United States Patent
Wolter et al.

(10) Patent No.: US 6,743,606 B1
(45) Date of Patent: Jun. 1, 2004

(54) PROCESSIVE SUGAR TRANSFERASE

(75) Inventors: Frank P. Wolter, Hamburg (DE); Petra Jorasch, Hamburg (DE); Ernst Heinz, Hamburg (DE); Ulrich Zähringer, Ahrensburg (DE)

(73) Assignees: Gesellschaft Für Erwerb und Verwertung von Schutzrechten-GVS mbH, Bonn (DE); Forschungszentrum Borstel, Borstel (DE)

( * ) Notice: Subject to any disclaimer, the term of this patent is extended or adjusted under 35 U.S.C. 154(b) by 0 days.

(21) Appl. No.: 09/668,788

(22) Filed: Sep. 22, 2000

Related U.S. Application Data

(63) Continuation-in-part of application No. PCT/DE99/00857, filed on Mar. 25, 1999.

(30) Foreign Application Priority Data

Mar. 25, 1998 (DE) .......................... 198 13 017
May 5, 1998 (DE) .......................... 198 19 958

(51) Int. Cl.[7] .......................... C12P 19/18; C12N 9/10; C12N 1/20; C12N 5/04; C07H 21/04

(52) U.S. Cl. .......................... 435/97; 435/4; 435/41; 435/69.1; 435/183; 435/193; 435/252.3; 435/254.11; 435/254.2; 435/410; 435/320; 435/419; 536/23.2; 536/23.7

(58) Field of Search .......................... 435/4, 41, 69.1, 435/97, 183, 193, 252.3, 254.11, 320, 410, 419; 536/23.2, 23.7

(56) References Cited

U.S. PATENT DOCUMENTS 5,545,553 A 8/1996 Gotschlich
5,641,668 A 6/1997 Berger et al.

OTHER PUBLICATIONS

Sorokin et al. SwissProt Database, Accession No. P54166, Oct. 1, 1996.*
Kunst et al. PIR Database, Accession No. C69935, Dec. 5, 1997.*
Koyama et al., "Parallel–up structure evidences the molecular directionality during biosynthesis of bacterial cellulose," Proc. Natl. Acad. Sci. USA, 94: 9091–9095 (1997).
Altschul, S. F., Gish, W., Miller, W., Myers, E. W., and Lipman, D. J., J. Mol. Biol., 215:403–410, 1990, "Basic Local Alignment Search Tool."
Bruzik, K., Jiang, R.–T., and Tsai, M.–D., Biochemistry, 22:2478–2488, 1983, "Phospholipids Chiral at Phosphorus: Preparation and Spectral Properties of Chiral Thiophospholipids."
Cutting, et al., in Molecular Biological Methods for Bacillus, p. 65, 1989, Harwood, C. R., and Cutting, S. M. (eds.), John Wiley & Sons.

Higgins, D. G., and Sharp, P. M., Gene, 73:237–244, 1988, "Clustal: A Package for Performing Multiple Sequence Alignment on a Microcomputer."
Ichikawa, Y., and Igarashi, Y., Tetrahedron Letters, 36:4585–4586, 1995, "An Extremely Potent Inhibitor for β–Galactosidase."
Jorasch, P., Wolter, F. P., Zähringer, U., and Heinz, E., Molecular Microbiology, 29(2):419–430, 1998, "A UDP Glucosyltransferase from Bacillus subtilis Successively Transfers Up to Four Glucose Residues to 1,2–Diacylglycerol: Expression of ypfP in Escherichia coli and Structural Analysis of Its Reaction Products."
Kates, M., in Glycolipids, Phosphoglycolipids, and Sulfoglycolipids, p. 1–109, 1990, Plenum Press.
Laemmli, U. K., Nature, 227:680–685, 1970, "Cleavage of Structural Proteins During the Assembly of the Head of Bacteriophage T4."
Linscheid, M., Diehl, B. W. K., Övermöhle, M., Riedl, I., and Heinz, E., Biochim. Biophys. Acta, 1347:151–163, 1997, "Membrane Lipids of Rhodopseudomonas viridis."
Ludovice, A. M., Wu, S. W., and deLencastre, H., Microbial Drug Resistance, 4(2):85–90, 1998, "Molecular Cloning and DNA Sequencing of the Staphylococcus aureus UDP–N–Acetylmuramyl Tripeptide Synthetase (murE) Gene, Essential for the Optimal Expression of Methicillin Resistance."
Price, K. D., Roels, S., and Losick, R., Journal of Bacteriology, 179(15):4959–4961, 1997, "A Bacillus subtilis Gene Encoding a Protein Similar to Nucleotide Sugar Transferases Influences Cell Shape and Viability."
Roughan, P. G., and Beevers, H., Plant Physiol., 67:926–929, 1981, "Effects of Cyanide on Rates and Products of Fatty Acid Synthesis by Chloroplasts Isolated from Spinacia oleracea."
Saxena, I. M., Brown, R. M. Jr., Fevre, M., Geremia, R. A., and Henrissat, B., Journal of Bacteriology, 177(6):1419–1424, 1995, "Multidomain Architecture of β–Glycosyl Transferases: Implications for Mechanism of Action."
Shimojima, M., Ohta, H., Iwamatsu, A., Masuda, T., Shioi, Y., and Takamiya, K., Proc. Natl. Acad. Sci., 94:333–337, 1997, "Cloning of the Gene for Monogalactosyldiacylglycerol Synthase and its Evolutionary Origin."

(List continued on next page.)

Primary Examiner—Manjunath Rao
(74) Attorney, Agent, or Firm—Knobbe, Martens, Olson & Bear, LLP

(57) ABSTRACT

The invention relates to a protein which presents identical or different catalytically active domains of glycosyltransferases and has a processive action. In particular, the same protein is successively active in at least two successive process steps.

6 Claims, 13 Drawing Sheets

OTHER PUBLICATIONS

Vaccaro, A. M., Tatti, M., Ciaffoni, F., Salvioli, R., Barca, A., and Roncaioli, P., *Biochim. Biophys. Acta,* 1149(1):55–62, 1993, "Studies on Glycosylceramidase Binding to Phosphatidylserine Liposomes: The Role of Bilayer Curvature."

Vanderjagt, D. J., Fry, D. E., and Glew, R. H., *Biochem. J.,* 300: 309–315, 1994, "Human Glucocerebrosidase Catalyses Transglucosylation Between Glucocerebroside and Retinol."

Yanisch–Perron, C., Vieira, J., and Messing, J., *Gene,* 33:103–119, 1985, "Improved M13 Phage Cloning Vectors and Host Strains: Nucleotide Sequences of the M13mp18 and pUC19 Vectors."

* cited by examiner

PL1

PL2

MGlcD 1

DGlcD 2

TGlcD 3

TeGlcD 4

R = R' = 16:0, 16:1, 18:0, 18:1

PL1
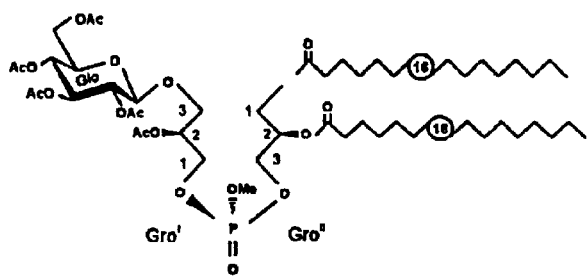
Figure 13
PL1'
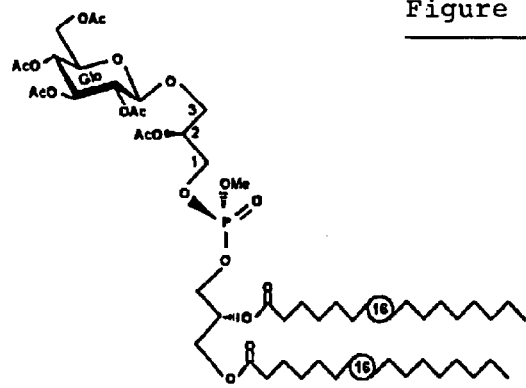
PL2
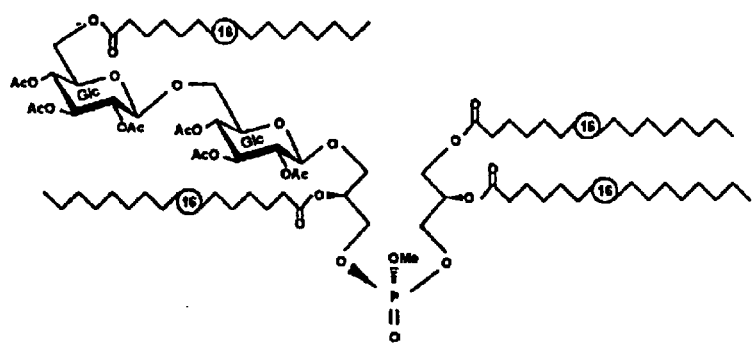
PL2'

SEQUENCE LISTING

<160> NUMBER OF SEQ ID NOS: 4

<210> SEQ ID NO 1
<211> LENGTH: 1149
<212> TYPE: DNA
<213> ORGANISM: Bacillus subtilis

<400> SEQUENCE: 1

```
ttgaataccamatamagagt attaattttg actgcaaatt acggaaatgg acatgtgcag     60
gtagccaaaa cactttatga acaatgtgta cggctcggct ttcagcatgt aacagtttct    120
aatttgtacc aagagtcaaa tccgattgtt tcagaggtaa ctcaatacct ttatttaaaa    180
agcttctcaa tcgggaaaca gttttatcgt ttgttttatt acggagttga caaaatctat    240
aataaacgta aattcaatat ttactttaaa atgggtaata aaagattggg cgaacttgtc    300
gatgaacatc agcccgatat tattattaat acatttccga tgatcgtcgt gccggaatac    360
agacgccgaa ctggaagagt cattcctacc ttcaacgtta tgactgattt ttgtcttcat    420
aaaatttggg ttcacgaaaa cgtggataaa tattatgtgg cgacagatta cgtgaaggaa    480
aaactgctgg agatcggcac tcatccaagc aatgtaaaaa tcacaggaat tccaatcagg    540
ccgcaatttg aagaatccat gcctgttggc ccgatatata aaaagtacaa tctttcacca    600
aacaaaaaag tgcttctgat catggcaggt gctcacggtg tattaaagaa cgtaaaagag    660
ctgtgcgaaa accttgtcaa ggatgaccaa gtgcaagtag ttgtcgtgtg cgggaaaaat    720
acggctttaa aagaatcttt gagtgcgctt gaagcggaaa atggtgacaa attaaaagtt    780
ctgggctatg tggagcgcat tgatgagcta tttcggatca cagattgcat gattaccaag    840
cccggcggca ttactttgac agaagccaca gccattggag tgcctgtcat tctgtacaaa    900
cccgtgcctg gccaggaaaa agaaatgca aacttctttg aagaccgcgg agctgccatc    960
gttgtgaacc gtcatgaaga gattctcgag tcagtcactt cccttcttgc agatgaagat   1020
accttgcatc gcatgaagaa aaacattaag gaccttcatt tagcaaactc ctctgaagtg   1080
attttagagg atatcctgaa ggaatcagaa atgatgaccg ccaaacaaaa agccaaagtg   1140
ctatcgtaa                                                           1149
```

```
<210> SEQ ID NO 2
<211> LENGTH: 382
<212> TYPE: PRT
<213> ORGANISM: Bacillus subtilis

<400> SEQUENCE: 2

Met Asn Thr Asn Lys Arg Val Leu Ile Leu Thr Ala Asn Tyr Gly Asn
 1               5                  10                  15

Gly His Val Gln Val Ala Lys Thr Leu Tyr Glu Gln Cys Val Arg Leu
                20                  25                  30

Gly Phe Gln His Val Thr Val Ser Asn Leu Tyr Gln Glu Ser Asn Pro
            35                  40                  45

Ile Val Ser Glu Val Thr Gln Tyr Leu Tyr Leu Lys Ser Phe Ser Ile
 50                  55                  60

Gly Lys Gln Phe Tyr Arg Leu Phe Tyr Tyr Gly Val Asp Lys Ile Tyr
 65                  70                  75                  80

Asn Lys Arg Lys Phe Asn Ile Tyr Phe Lys Met Gly Asn Lys Arg Leu
                85                  90                  95

Gly Glu Leu Val Asp Glu His Gln Pro Asp Ile Ile Ile Asn Thr Phe
            100                 105                 110

Pro Met Ile Val Val Pro Glu Tyr Arg Arg Arg Thr Gly Arg Val Ile
            115                 120                 125

Pro Thr Phe Asn Val Met Thr Asp Phe Cys Leu His Lys Ile Trp Val
130                 135                 140

His Glu Asn Val Asp Lys Tyr Tyr Val Ala Thr Asp Tyr Val Lys Glu
145                 150                 155                 160

Lys Leu Leu Glu Ile Gly Thr His Pro Ser Asn Val Lys Ile Thr Gly
                165                 170                 175

Ile Pro Ile Arg Pro Gln Phe Glu Glu Ser Met Pro Val Gly Pro Ile
            180                 185                 190

Tyr Lys Lys Tyr Asn Leu Ser Pro Asn Lys Lys Val Leu Leu Ile Met
            195                 200                 205

Ala Gly Ala His Gly Val Leu Lys Asn Val Lys Glu Leu Cys Glu Asn
            210                 215                 220

Leu Val Lys Asp Asp Gln Val Gln Val Val Val Cys Gly Lys Asn
225                 230                 235                 240

Thr Ala Leu Lys Glu Ser Leu Ser Ala Leu Glu Ala Glu Asn Gly Asp
                245                 250                 255

Lys Leu Lys Val Leu Gly Tyr Val Glu Arg Ile Asp Glu Leu Phe Arg
            260                 265                 270

Ile Thr Asp Cys Met Ile Thr Lys Pro Gly Gly Ile Thr Leu Thr Glu
            275                 280                 285

Ala Thr Ala Ile Gly Val Pro Val Ile Leu Tyr Lys Pro Val Pro Gly
290                 295                 300

Gln Glu Lys Glu Asn Ala Asn Phe Phe Glu Asp Arg Gly Ala Ala Ile
305                 310                 315                 320

Val Val Asn Arg His Glu Glu Ile Leu Glu Ser Val Thr Ser Leu Leu
                325                 330                 335

Ala Asp Glu Asp Thr Leu His Arg Met Lys Lys Asn Ile Lys Asp Leu
            340                 345                 350

His Leu Ala Asn Ser Ser Glu Val Ile Leu Glu Asp Ile Leu Lys Glu
            355                 360                 365

Ser Glu Met Met Thr Ala Lys Gln Lys Ala Lys Val Leu Ser
            370                 375                 380
```

<210> SEQ ID NO 3
<211> LENGTH: 975
<212> TYPE: DNA
<213> ORGANISM: Staphylococcus aureus

<400> SEQUENCE: 3

| | |
|---|---|
| atggttactc aaataaaaa gatattgatt attactggct cattcggtaa cggtcatatg | 60 |
| caagttacac agagtatcgt taatcaactt aatgatatga atctagacca tttaagcgtc | 120 |
| attgagcacg atttatttat ggaagctcat ccaattttga cttctatttg taaaaaatgg | 180 |
| tatatcaata gctttaaata ttttagaaat atgtacaaag ggttttatta cagccgccca | 240 |
| gataaactag acaaatgttt ttacaaatac tatggactta ataagttaat taatttattg | 300 |
| ataaaagaaa agccagattt aatattatta cgtttccta caccagttat gtcggtacta | 360 |
| actgagcaat ttaacattaa tattccagtt gctacagtga tgacagacta tcgcttacat | 420 |
| aaaaactgga ttacgccgta ttcaacaaga tattatgtgg caacaaaaga aacgaaacaa | 480 |
| gacttcatag acgtaggtat tgatccttca acagttaaag tgacaggtat tcctattgat | 540 |
| aacaaatttg aaacgcctat taatcaaaag cagtggttaa tagacaacaa cttagatcca | 600 |
| gataagcaaa ctattttaat gtcagctggt gcatttggtg tatctaaagg ttttgacacg | 660 |
| atgattactg atatattagc gaaaagtgca atgcacaag tagttatgat ttgtggtaag | 720 |
| agcaaagagc taaagcgttc tttaacagct aagtttaaat taacgagaat gtatttgatt | 780 |
| ctaggttata ccaaacacat gaatgaatgg atggcatcaa gtcaacttat gattacgaaa | 840 |
| cctggtggta tcacaataac tgaaggtttc gcccgttgta ttccaatgat tttcctaaat | 900 |
| cctgcacctg gtcaagagct tgaaaatgcc tttactttg aagaaaaagg ttttggtaaa | 960 |
| acgctgatac tccag | 975 |

<210> SEQ ID NO 4
<211> LENGTH: 391
<212> TYPE: PRT
<213> ORGANISM: Staphylococcus aureus

<400> SEQUENCE: 4

Met Val Thr Gln Asn Lys Lys Ile Leu Ile Ile Thr Gly Ser Phe Gly
1               5                   10                  15

Asn Gly His Met Gln Val Thr Gln Ser Ile Val Asn Gln Leu Asn Asp
            20                  25                  30

Met Asn Leu Asp His Leu Ser Val Ile Glu His Asp Leu Phe Met Glu
        35                  40                  45

Ala His Pro Ile Leu Thr Ser Ile Cys Lys Lys Trp Tyr Ile Asn Ser
    50                  55                  60

Phe Lys Tyr Phe Arg Asn Met Tyr Lys Gly Phe Tyr Tyr Ser Arg Pro
65                  70                  75                  80

Asp Lys Leu Asp Lys Cys Phe Tyr Lys Tyr Gly Leu Asn Lys Leu
                85                  90                  95

Ile Asn Leu Leu Ile Lys Glu Lys Pro Asp Leu Ile Leu Leu Thr Phe
            100                 105                 110

Pro Thr Pro Val Met Ser Val Leu Thr Glu Gln Phe Asn Ile Asn Ile
        115                 120                 125

Pro Val Ala Thr Val Met Thr Asp Tyr Arg Leu His Lys Asn Trp Ile
    130                 135                 140

Thr Pro Tyr Ser Thr Arg Tyr Tyr Val Ala Thr Lys Glu Thr Lys Gln
145                 150                 155                 160

-continued

```
Asp Phe Ile Asp Val Gly Ile Asp Pro Ser Thr Val Lys Val Thr Gly
            165                 170                 175

Ile Pro Ile Asp Asn Lys Phe Glu Thr Pro Ile Asn Gln Lys Gln Trp
            180                 185                 190

Leu Ile Asp Asn Asn Leu Asp Pro Asp Lys Gln Thr Ile Leu Met Ser
            195                 200                 205

Ala Gly Ala Phe Gly Val Ser Lys Gly Phe Asp Thr Met Ile Thr Asp
        210                 215                 220

Ile Leu Ala Lys Ser Ala Asn Ala Gln Val Val Met Ile Cys Gly Lys
225                 230                 235                 240

Ser Lys Glu Leu Lys Arg Ser Leu Thr Ala Lys Phe Lys Leu Thr Arg
                245                 250                 255

Met Tyr Leu Ile Leu Gly Tyr Thr Lys His Met Asn Glu Trp Met Ala
            260                 265                 270

Ser Ser Gln Leu Met Ile Thr Lys Pro Gly Gly Ile Thr Ile Thr Glu
        275                 280                 285

Gly Phe Ala Arg Cys Ile Pro Met Ile Phe Leu Asn Pro Ala Pro Gly
        290                 295                 300

Gln Glu Leu Glu Asn Ala Phe Tyr Phe Glu Glu Lys Gly Phe Gly Lys
305                 310                 315                 320

Ile Ala Asp Thr Pro Glu Glu Ala Ile Lys Ile Val Ala Ser Leu Thr
                325                 330                 335

Asn Gly Asn Glu Gln Leu Thr Asn Met Ile Ser Thr Met Glu Gln Asp
            340                 345                 350

Lys Ile Lys Tyr Ala Thr Gln Thr Ile Cys Arg Asp Leu Leu Asp Leu
            355                 360                 365

Ile Gly His Ser Ser Gln Pro Gln Glu Ile Tyr Gly Lys Val Pro Leu
        370                 375                 380

Tyr Ala Arg Phe Phe Val Lys
385                 390
```

PROCESSIVE SUGAR TRANSFERASE

This application is a Continuation-in-Part of International Application No. PCT/DE99/00857, filed on Mar. 25, 1999, which claims priority to German Patent No. 198 13 017.1, filed Mar. 25, 1998 and German Patent No. 198 19 958.9, filed May 5, 1998. The disclosure of these applications are hereby incorporated by reference in their entirety.

FIELD OF THE INVENTION

The invention relates to the use of processive UDP-sugar: 1,2-diacylglycerol-3-β-, UDP-sugar: 3-β-1,3'-phospho-sn-glycerol-1',2'-diacyl-sn-glycerol)- and UDP-sugar: 3-[O-β-D-glucopyrartosyl]-sn-glycerol-1,3 '-phospho-1',2'-diacyl-sn-glycerol-D-sugar transferases and similar proteins as well as the corresponding coding nucleic acids for the manipulation of the contents and/or the structure of glycosyldiacylglycerols and/or the synthetic secondary products thereof, as well as other substrates which are glycosylated by these enzymes, in transgenic cells and/or organisms.

Glycosyldiacylglycerols were produced enzymatically by means of a sugar transferase (glycosyl transferase). For this purpose, the gene coding for a UDP-sugar transferase was isolated from genomic DNA of *Bacillus subtilis* and *Staphylococcus aureus*, and cloned into, and expressed in, *E. coli*. The activity of the enzymes was confirmed by means of specific in vitro-enzyme assays. The products were also detected and identified in lipid extracts of transgenic *E. coli* cells. The products are various novel glycolipids having different number of glucose residues (maximum of 4) linked via a β(1→6)glycosidic bond, and utilizing diacylgylcerol (DAG) or phosphatidylglycerol (PG) as the primary acceptor.

In addition, these novel glycolipids comprise two differently structured novel phosphoglycolipids (PL1 and PL2) with a different number of glucose residues (maximum of two) which in the case of (PL2) are also linked via a β(1→6)glycosidic bond and utilize phosphatidylglycerol as the acceptor (i.e. both diastereomers, i.e. with respect to the configuration of the non-acylated glycerol residue). The glycosyl residues may further be acylated in position 6''' of the terminal glucose:

1) MGlcD: 3-[O-β-D-glucopyranosyl]-1,2-diacylglycerol (*Staphylococcus aureus* ypfP)
2) DGlcD: 3-[O-β-D-glucopyranosyl-(1→6)-O-β-D-glucopyranosyl]-1,2-diacylglycerol
3) TGlcD: 3-[O-β-D-glucopyranosyl-(1→6)-O-β-D-glucopyranosyl-(1→6)-O-β-D-glucopyranosyl]-1,2-diacylglycerol
4) TeGlcD: 3-[O-β-D-glucopyranosyl-(1→6)-O-β-D-glucopyranosyl-(1→6)-O-β-D-glucopyranosyl-(1→6)-O-β-D-glucopyranosyl]-1,2-diacylglycerol
5) Phospholipid 1:3-[O-β-D-glucopyranosyl]-sn-glycerol-1,3'-phospho-1',2'-diacyl-sn-glycerol)
6) Phospholipid 2:{3-[O-(6'''-O-acyl)-β-D-glucopyranosyl-(1'''6')-O-β-D-glucopyranosyl]-2-acyl-sn-glycerol-1,3'-phospho-1',2'-diacyl-sn-glycerol}

Note: The numbering of the glycerol residues I (Gro') and II (Gro'') corresponds herein to the numbering 1–3 and 1'–3', respectively, i.e. Gro' is "left-hand" and Gro'' is "right-hand" in accordance with FIG. 13.

Surprisingly, the enzymes act in a processive manner, i.e. all detected novel glycolipids are formed by successive addition of UDP-glucose to the respective preceding product of the enzymes. Further, alkyl-β-D-glucosides, ceramides (both enzymes), sterols and sterol glucosides (only the enzyme of *S. aureus*) are used as acceptors for a further glucosylation reaction.

DETAILED DESCRIPTION

Glyceroglycolipids represent a group of membrane components which are very hetero-geneous with respect to their structure. They are found in bacteria (Kates, 1990), plants and in very low amounts also in animals. Many structures especially of bacterial glycolipids have already been described many years ago (Kates, 1999), however, none of the genes synthesizing these glycolipids have been cloned, so that these substances can be obtained from the corresponding organisms only in analytical amounts. Only at the beginning of 1997 was the first publication issued, wherein the cloning and expression of a plant galactose: 1,2-diacylglycerol galactosyl transferase is described (Shimojina et al., 1997). However, this enzyme is no "processive" glycosyl transferase.

Database searches in the "U.S. Patent Database" revealed that two further patents relating to glycosyl transferases exist: U.S. Pat. No. 5,545,554: Glycosyl transferases for biosynthesis of oligosaccharides, and genes and encoding them, and U.S. Pat. No. 5,641,668: Proteins having glycosyl transferase activity. It appears that the first-mentioned patent only relates to glycosyl transferases which synthesize oligosaccharide, so that this patent is not relevant with respect to the enzyme, viz a lipid glycosyl transferase, described herein. The second-mentioned patent relates to glycosyl transferases in general, in view of which the processive enzyme described in this specification is novel.

BRIEF DESCRIPTION OF THE FIGURES

Glycosyl diacylglycerols are naturally occurring compounds found in plants, animals and bacteria. However, an inexpensive, large-scale production of these compounds was not possible so far, since corresponding genes were not yet cloned. Glycosyl diacylglycerols can be used in a variety of applications, depending on the number of sugar residues and the structure of the fatty acids.

When esterified with usual C18 unsaturated fatty acids, diglucosyl diacylglycerols have emulsifier properties which are useful in food industrial applications (in mayonnaise, margarine, ice cream, confectionery etc.).

Figure 1:
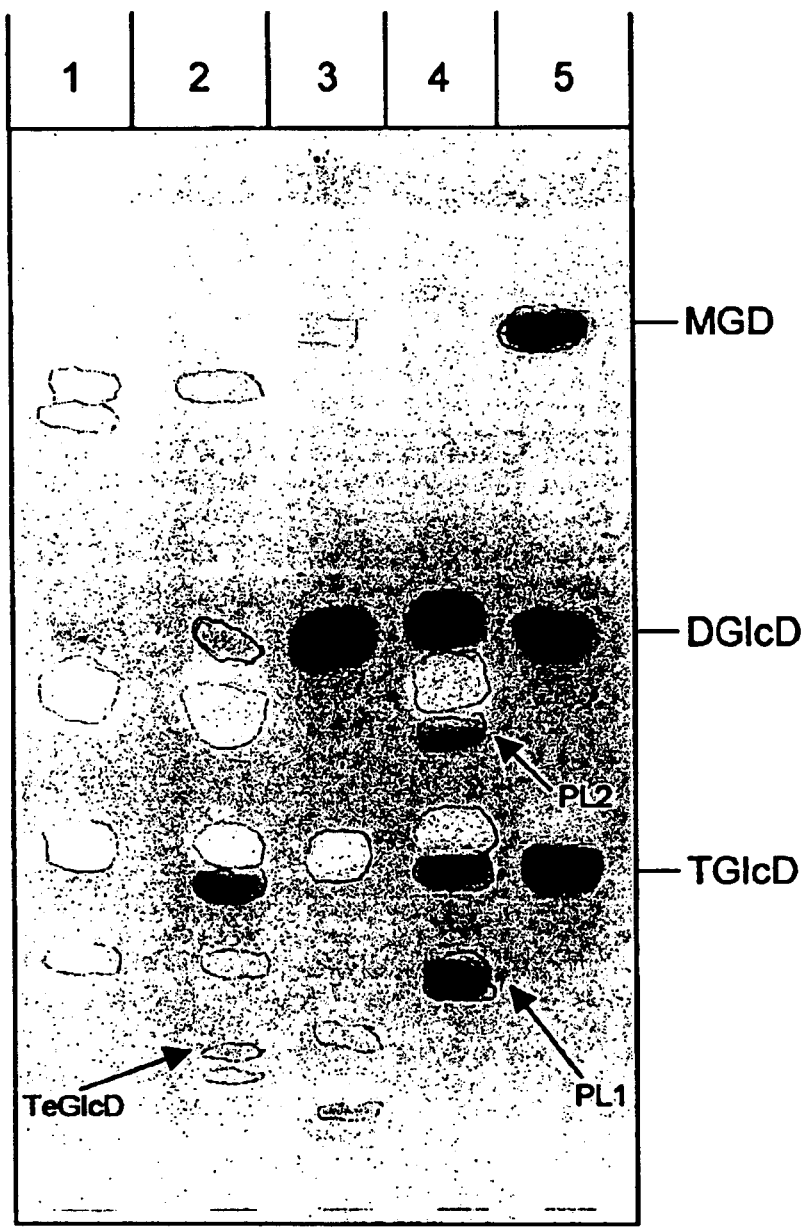

In the presence of highly unsaturated fatty acids, glycolipids may be introduced into polymers, which then obtain new characteristics and surfaces. Finally, glycosyl diacylgylcerols may obtain detergent characteristics, when the fatty acid chain length is drastically shortened. This would already now be possible in transgenic rape seed with predominant lauric acid. Such detergents could be produced in large amounts in an inexpensive manner, and such detergents would be biologically degradable.

The phospholipids which are glucosylated by the enzyme of *S. aureus* receive new physico-chemical characteristics due to the charge of the phosphate residue between the two glycerol residues on the one hand, and on the other hand due to acylation of the sugar residue(s). Thus, by use of the described processive sugar transferases, not only neutral lipids, but also charged glycolipids can be specifically produced and varied. Thus, a further class of charged glycophospholipids are developed via the sugar transferases.

In the production of plant oils from oil seeds, a lecithin fraction is obtained, wherein phospholipids and glycolipids are accumulated. By over-expressing the genes disclosed in this specification in these plants, a variety of glycolipids (glucosyl diacylglycerols, steryl glucoside, glucocerebroside and other lipids described herein) could be concentrated, with a favourable effect on the baking properties of bakery products, to which the lecithin fraction is added.

In addition, the phospholipids glucosylated by the *S. aureus* enzyme receive further physicochemical properties due to the charge of the phosphate residue.

This invention, therefore, relates to a process for the production of glycolipids in transgenic cells and/or organisms, comprising the following steps:

transfer of a nucleic acid molecule that codes for a protein having the biological activity of a processive diacylglycerol glycosyltransferase to the cells or organism, expression of the protein having a biological activity of a processive diacylglycerol glycosyltransferase under suitable regulatory sequences in the cells or the organism, and if desired, recovery of the glycolipids synthesized by the biological activity of a processive diacylglycerol glycosyltransferase from the cells or the organism.

In a preferred embodiment of the invention, the nucleic acid molecule codes for a protein having the biological activity of a processive diacylglycerol glycosyltransferase from *Bacillus subtilis* or *Staphylococcus aureus*.

The transgenic cells may be any cells that are useful for the production of the new glycolipids, preferably the cells are plant, yeast or bacteria cells. The transformed organism is preferably a plant, yeast or bacterium.

As mentioned above and as will be clear from the following description, the glycolipids produces by the process of the invention are preferably glycosyl diacylglycerols and/or phosphoglycolipids. More preferably, the glycolipids are monoglycosyldiacylglycerol, diglycosyldiacylglycerol, triglycosyl diacylglycerol, tetraglycosyldiacylglycerol, glycosyl ceramide, diglycosyl ceramide, steryl glycoside, steryl diglycoside, glycosyl phosphatidylglycerol, and/or diglycosyl phosphatidylglycerol. Most preferably, the glycolipids are monoglucosyldiacylglycerol, diglucosyldiacylglycerol, triglucosyldiacylglycerol, tetraglucosyldiacylglycerol, glucosyl ceramide, diglucosyl ceramide, steryl glucoside, steryl diglucoside, glucosyl phosphatidylglycerol, and/or diglucosylphosphatidylglycerol.

The invention is also directed to the use of a nucleic acid molecule coding for a protein having the biological activity of a processive diacylglycerol glycosyltnsferase or of a proteins having the biological activity of a processive diacylglycerol glycosyltransferase for processive glycosylation, in particular for production of glycolipids. Processive glycosylation, in particular the production of glycolipids, may take place in vivo or in vitro.

Further, the invention is directed to tetraglucosyldiacylglycerol, synthesized and described herein for the first time. The same applies to glucosylphosphatidylglycerol and diglucosylphosphatidylglycerol.

The invention is further directed to the use of the glycolipids produced by processive glycosylation according to the invention in the food industry, as an emulsifier or as a detergent.

A processive glycosyl transferase, as described herein, catalyzes the successive transfer of one or more hexose residues to an acceptor molecule. In particular the enzyme catalyzes at least one of the following reactions:

a) addition of hexose β(1→6) to diacylglycerol,
b) addition of hexose β(1→6) to a MHexD,
c) addition of hexose β(1→6) to a DHexD,
d) addition of hexose β(1→6) to a THexD,
e) addition of hexose β(1→6) to a TeHexD,
f) addition of hexose β to a ceramide,
g) addition of hexose β(1→6) to a monohexosyl ceramide,
h) addition of hexose β to a sterol,
i) addition of hexose β(1→6) to a steryl glucoside,
j) addition of hexose in β-glycosidic linkage to the primary hydroxyl group of phosphatidylglycerol,
k) addition of hexose β(1→6) to the first hexose of phosphatidylglycerol-β-D- glucoside.

In paricular the glycosyl transferase catalyzes the successive transfer of one or more hexose residues to at least one acceptor molecule for synthesis of glycolipids, in particular phosphoglycolipids, in particular catalyzing one of the following reactions:

a) addition of Glc β(1→6) to a diacylglycerol,
b) addition of Glc β(1→6) to a MGlcD,
c) addition of Glc β(1→6) to a DGlcD,
d) addition of Glc β(1→6) to a TGlcD,
e) addition of Glc β(1→6) to a TeGlcD,
f) addition of Glc β to a ceramide,
g) addition of Glc β(1→6) to a monoglucosyl ceramide,
h) addition of Glc β to a sterol,
i) addition of Glc β(1→6) to a steryl glucoside,
j) addition of Glc in β-(1→6)-glycosidic linkage to the primary hydroxyl group of phosphatidylglycerol,
k) addition of Glc β(1→6) to the first Glc of phosphatidylglycerol-β-D-glucoside.

The invention also relates to the DNA sequences coding for an protein having enzyme activity of a processive glycosyl transferase from *Bacillus subtilis* and/or *Staphylococcus aureus*. Further the invention is directed to DNA sequences coding for a protein which shows at least 50%, preferably at least 70%, more preferably at least 90%, and most preferably at least 95% identity with the deduced protein of ypfP (Clustal X). More particular, the DNA sequence codes for a protein having more than 5 amino acids within the amino acid sequence EHQPDIII (SEQ ID NO. 5) which are identical with the amino acid sequence of the proteins from *B. subtilis* and/or *S. aureus*, preferably having more than 6 amino acids within the amino acid sequence QVVVVCGKN (SEQ ID NO. 6) or the amino acid sequence DCMITKPG (SEQ ID NO. 7) which are identical with the amino acid sequence of the proteins from *B. subtilis* and/or *S. aureus*. More preferably, the DNA sequence codes for a protein the amino acid sequence of which comprises the amino acid sequence MITKPGGITxTE (SEQ ID NO. 8) (wherein x is any amino acid), or the amino acid sequence VKxTGIPI (SEQ ID NO. 9) (wherein x is any AA) or the amino acid sequence of which comprises more than 5 amino acids within the sequence ZPDIIIxxxP (SEQ ID NO. 10) (wherein Z represents the amino acid Q or K and x is any amino acid) which are identical to the sequence found in *Bacillus subtilis* and/or *Staphylococcus aureus*.

The invention also relates to the use of a processive glycosyltransferase for biosynthetic production of glycolipids having the following structure:

a) β-D-Glcp-(1→6)-β-D-Glcp-(1→6)-β-D-Glcp-(1→6)-β-D-Glcp-(1→6)-Gro,
b) 3-[O-β-D-Glucopyranosyl]-phosphatidylglycerol (PL1), or c) {3-[O-(6'''-O-acyl)-β-D-glucopyranosyl-(1'''→6'')-O-β-D-glucopyranosyl]-2-acyl-phosphatidylglycerol} (PL2).

Finally, the invention is directed to secondary products which are produced by biosynthetically and gentechnically engineered microorganisms and/or plants using a processive glycosyl transferase by further conversion of the products produced by the action of the processive sugar transferases, in particular by addition of a fatty acid to the position 6''' of the terminal hexose in {3-[O-β-D-glucopyranosyl-(1'''→6'')-O-β-D-glucopyranosyl]-2-acyl-phosphatidylglycerol}.

PL1, PL2 and their respective diastereomeric counterparts are illustrated in FIG. 13. PL1' is the diastereomeric counterpart of PL1 and PL2' is the diastereomeric counterpart of PL2.

1. Isolation and Cloning of ypfP

The ypfP gene was isolated from *B. subtilis*, the gene being described in the SubtiList Database as an open reading frame of unknown function (accession number P54166). The other gene that was isolated and cloned was a sequence from *Staphylococcus aureus* (accession number Y14370) described as an open reading frame of unknown function.

For DNA isolation, restriction analysis and ligation, standard techniques were used (Sambrook et al., 1989). Genomic DNA from *Bacillus subtilis* 019 was isolated according to Cutting et al., 1990. Genomic DNA of *S. aureus* was provided by Prof. Dr. Witte, (Robert Koch-Institute, Postfach 650280, 13302 Berlin). Restriction endonucleases and DNA-modifying enzymes were purchased from New England Biolabs and Boehringer Mannheim, and used as recommended by the suppliers.

*E. coli* XL1 Blue (MRF') (Stragene), *E. coli* BL21 (DE3) (Novagen) and *Bacillus subtilis* 019 were grown at 37° C. in a Luria Broth (LB) (Sambrook et al., 1989). For plasmid-bearing *E. coli* strains, the antibiotics ampicillin (100 μg ml) and kanamycin (30 μg ml) were included in the medium. The vectors pUC18 (Yanish-Perron et al., 1985) and pET24c(+) and pET24d(+) (Novagen) were used as cloning vectors. The ypfP genes were isolated from genomic DNA of *B. subtilis* and *S. aureus* by PCR. For this purpose the specific primers PJ1 (5'-CCGAGCTCCCATATGAATACCAATAAAAGAG 3') (SEQ ID NO. 11) and PJ2 (5' TCCGGATCCTTACGATAGCACTTTGGC 3') (SEQ ID NO. 12) for *B. subtilis* ypfP and the primers PJ10 5' TTCCATGGTTACTCAAAATAAAAAGATATTG 3' (SEQ ID NO. 13) and PJ11 5' TTTGGATCCTTATTTAACGAAGAATCTTGCATATAA 3' (SEQ ID NO. 14) for the *S. aureus* gene (say) were used, the underlined part of which annealed to the 5' and 3' end of the ypfP/say genes. The following amplification program was used: 10 min at 94° C.; 30 cycles of 0.5 min at 55° C. and 60° C. for *S. aureus* ypfP, respectively, 2 min at 72° C., 1 min at 94° C.; one cycle of 10 min at 74° C., Pwo-polymerase (Boehringer) was used for the amplification of the 1170 bp product of the genomic DNA of *B. subtilis*, Pfu-polymerase (Stratagene) was used for the amplification of the 1190 bp product from *S. aureus* genomic DNA. The amplified genes were cloned into SmaI-linearized pUC18 vector, resulting in pypfP3 and psay1. For construction of the expression vectors pEypfP 24 and pEsay24, the ypfP fragments were released by BamHI and NdeI and NcoI digestion, respectively, from pypfP3 and psay1, and inserted into BamHi-, NdeI- and NcoI-linearized pET24c(+) and pET24d(+), respectively. *E. coli* XL1 Blue (MRF') was transformed with pypfP3 and psay1 and *E. coli* BL21 (DE3) was transformed with pEypfP24 and pEsay24. Correct in-frame cloning was confirmed by sequencing. One strand of the DNA of pypfP3 and psay1 was sequenced using the dideoxy method (automatic sequencer 373A and 377, Applied Biosystems). For computer analysis of the sequences, Clone manager for Windows 4.1 (Scientific and Educational Software) was used. Database searches were performed using the BLAST algorithm (Altschul et al., 1990). Sequence alignments were performed using Clustal X (Higgins and Sharp, 1988).

2. Expression of the ypfP/say-genes

For expression of the genes, ypfP was cloned into pET24c (+) and pET24d(+), respectively, and *E.coli* BL21 (DE3) was transformed with the resulting constructs pEypfP24 and pEsay24. Pre-cultures of *E. coli* BL21 (DE3), *E. coli* BL21 (DE3) pEypfP24 and *E. coli* BL21 (DE3) pEsay24 were grown overnight at 37° C., and expression cultures were started at an optical density (O.D.)$_{580}$ of 0.05. Induction was performed by adding 0.4 mM IPTG at an optical density of 0.8 and further incubation for 2 h at 37° C. All subsequent steps were carried out at 4° C. Cells were collected by centrifugation (15 min, 5000×g). The cell pellet was re-suspended in a buffer 1 (50 mM Tris-HCl, pH 8.0; 20% (v/v) glycerol) (4% of the volume of the expression culture). The cells were frozen and sonicated after thawing (3×40 s; Braun, Labsonic 2000). Inclusion bodies were collected by centrifugation (15 min, 4000×g) and the supernatant was then divided into the membrane fraction and the soluble supernatant (*B. subtilis* ypfP) by ultrasonification (1 h, 147000×g).

The inclusion bodies, the membrane fraction and the soluble supernatant were separated in an SDS-PAGE. The SDS-PAGE was carried out as described by Laemmli, 1970, and the gels were stained with Coomassie brilliant blue R250 (Serva).

By SDS-PAGE analysis, over-expression of a protein having an apparent molecular mass of 44 kDa could be identified in the membrane fraction and the inclusion body fraction. The molecular weight corresponds to the calculated mass of 43.6 kDa or 44.7 kDa, respectively, for YpfP. This protein was not present in the soluble fraction and in untransformed *E. coli*.

3. Lipid Extraction and Analysis

Expression cultures of *E. coli* BL21 (DE3) pEypjP24 and pfsay 24 and cultures of the late logarithmic growth stage of *Bacillus subtilis* 019 were harvested by centrifugation (15 min, 5000×g), and the sedimented cells boiled for 10 min in water. Lipid extraction was performed as described by Linscheid et al., 1997. For separation of individual lipids by preparative chromatography, the lipids were subjected to thin-layer chromatography in the following solvent systems: (1) chloroformn/methanol/H$_2$O (70:30:4. v/v/v) for separation of MGlcD, DGlcD, TGlcD and TeGlcD from phospholipids; (2) diethyl ether/petroleum ether (2:1, v/v) for separation of acetylated DGlcD from non-acetylated DGlcD; (3) diethyl ether/petroleum for separation of acetylated DGlcD from non-acetylated DGlcD; (3) diethyl ether/petroleum ether (4:1, v/v) for separation of acetylated TGlcD from non-acetylated TGlcD; (4) chloroform/acetone (9:1, v/v) for separation of acetylated TeGlcD from non-acetylated TeGlcD.

Separation of the two acetylated phosphoglucolipids PL1 and PL2 was performed in the solvent chloroform/methanol (80:20, v/v). Then both acetylated lipids were extractedfrom the silica gel and re-suspended in chloroform. The lipids were methylated by addition of diazomethane and subsequently separated in the solvent toluene/methanol (9:1, v/v).

Acetylation of the glycolipids was performed as described by Tulloch et al., 1973. Synthesis of the fatty acid methyl esters from DGlcD with sodium methylate was performed according to Roughan and Beevers, 1981. Release of the fatty acid from the sn 1 position of DGlcD was achieved by incubation with Rhizopus Lipase (Boehringer) according to suppliers' protocol. Incubation with Cerebrosidase (provided by Prof. Dr. Sandhoff, University Bonn) was performed as described by Vaccaro et al., 1993.

The lipid extracts of E. coli BL21 (DE3) pEypfP24 and pEsay24 showed various new glycolipids, which could not be detected in the wild-type (FIG. 1). These glycolipids reacted with a sugar-specific spray reagent, but they were ninhydrin and phosphate negative (the native PL1 and PL2 were phosphate positive). One of the glycolipids co-migrated with a diglucosyl diacylglycerol (DGlcD) standard of B. cereus. The different glycolipids were purified and acetylated. The glycolipid band with the polarity of DGlcD also co-migrated after acetylation with the acetylated DGlcD standard of B. cereus.

4. Analysis of the New Glycolipids by MS and NMR

Mass spectrometric (MS) and nuclear magnetic resonance spectroscopic (NMR) analysis of the new glycolipids was exclusively performed with the per-O-acetylated derivatives (1,2,3,4) and the phosphomethyl esters (PL1, PL2) of the glycolipids, respectively.

4.1. Mass Spectrometric Analysis (CI-MS and MALDI-MS)

4.4.1. EI-MS and CI-MS (DIP-mode)

Mass spectrometric analysis of the neutral glycolipids was carried out with a Hewlett Packard mass spectrometer (Model 5989) using the direct insert probe (DIP) mode. The sample was evaporated from 80° C. to 325° C. at a rate of 30° C./min.

While all per-O-acetylated di-(2), tri-(3) and tetrahexosyl-(4) diacylglycerolipids could be analyzed by MS analysis in the DIP mode directly, the two phospholipids PL1 and PL2 could not be analyzed by this technique. Due to the high polarity and the complexity of the molecule, the phospholipids were, therefore, dephosphorylated with hydrogen fluoride (48% HF, 4° C., 20 h) prior to MS analysis, the dephosphorylated fragment was per-O-acetylated and only after this treatment analyzed by mass spectrometry (DIP mode). Electron impact spectra (EI-MS) were recorded at 70 eV and chemical ionization spectra (CI MS) were obtained using ammonia (0.5 torr).

In the DIP MS analysis all per-O-acetylated di-(2), tri-(3) and tetrahexosyl-(4) diacylglycerolipids in the EI mode showed characteristic fragments for terminal mono-hexosyl (m/z=331) and di-hexosyl (m/z=619) residues and differed from each other in the evaporation rate maximum (9.5 min, 2, 10.6 min, 3 and 12.0 min, 4). The disaccharid 2 showed in the CI MS a pseudomolecular ion $[M+NH_4]^+$ at m/z=1202, wherein hexadecanoyl (16:0) and hexadecenoyl (16:1) could be identified as the fatty acid residues. In addition, a second ion $[M+NH_4]^+$ at m/z=1230 was observed, which could be identified as disaccharide with 16:0 and 18:1 (or 18:0 and 16:1) as fatty acids. The amounts of these differently acetylated diglycosyl lipids were present in a relative proportion of 2:3.

The trisaccharide 3 showed the expected pseudomolecular ion $[M+NH_4]^+$ at m/z=1490 and 1516 with the same heterogeneity in its acylation pattern, however in a slightly different proportion (2:1).

The tetrasaccharide 4 showed an evaporation profile with an increased maximum in the evaporation time (12.0 min) in comparison to 2 and 3. Pseudomolecular ions in the CI MS could not be produced with this compound. The presence of the tetrasaccharide 4 could, therefore, only be indirectly deduced under these conditions from the characteristic fragments of the non-reducing glycosyl residue (m/z=331 and 619, respectively).

In the DIP MS (CI mode) both PL1 and PL2 showed a characteristic biphasic evaporation profile, wherein the first maximum (~6 min) from the dephosphorylated and re-acetylated partial structures and the second maximum (~11 min) from the diagnostic pyrolysis fragments of the intact, not cleaved by HF hydrolysis phospholipids could be assigned. From this result it had to be noted that the applied reaction time (6–20 h) for removal of the phosphate residue with aqueous (48%) HF was not sufficient, since both phospholipids were cleaved only partially into their dephosphorylated partial fragments. In spite of this limitation, the fatty acid distribution pattern for both of the glycerol residues $Gro^I$ and $Gro^{II}$ could be unambiguously determined.

For PL1, the first peak revealed two pseudomolecular ions $[M+NH_4]^+$ at f/z=626 and 654, which could be assigned to the molecule ions and, thus, to the mono-acetylated glycerol residue $Gro^{II}$ with 16:0 and 16:1 (M=608) and a 16:0 and 18:1 (or 18:0 and 16:1) (M=636), respectively. Thus, this peak contained the expected product of the HF treatment and re-acetylation. In contrast, an analogous reaction product deduced from $Gro^I$ (with Glc as the substituent) was not observed.

The second peak (~11.0 min) revealed three fragments, which in contrast to the first peak represented only pyrolysis products of PL1, produced during MS analysis, but no intact derivatives. The first ion (m/z=447) was assigned to a fragment deduced from $Gro^I$, substituted with a peracetylated Glc and with an acetyl residue. The two other fragments (m/z=549 and 577) originate from $Gro^{II}$. They carried a diacylglycerol, wherein each a palmitic acid (16:0) and a palmitoleic acid (16:1) were esterified (m/z=549), and a second fragment (m/z=577) with each a palmitic acid (16:0) and an oleic acid (18:1) (alternatively 16:1 and 18:0). Already from this fragmentation pattern it could be concluded that PL1 is an "asymmetrically acylated" phospholipid, because $Gro^{II}$ carries both fatty acids, and $Gro^I$ in the native phospholipid with a free hydroxyl group and a glucose appears to be relatively hydrophilic.

The dephosphorylated and per-O-acetylated PL2 also showed a biphasic evaporation profile in the DIP MS analysis. The first peak had an evaporation maximum (~6 min) and a fragmentation pattern identical with PL1, indicating that PL2, is identical with PL1 with respect to the fatty acid substitution pattern in $Gro^{II}$. In contrast, the second peak (11.0 min) revealed four fragmentations. The first couple (m/z=550 and 577) was identified as a pyrolysis fragment deduced from $Gro^{II}$ with 16:0 and 18:1 (16:1 and 18:0, respectively) and was therefore analogous to PL1. The second couple (m/z=1202.9 and 1231.1) could be identified as $[M+NH_4]^+$ ion of an intact derivative, produced from PL2 after de-phosphorylation and re-acetylation. This PL2 derivative is a diglucosyl diacylglycerol being further esterified with two fatty acids 16:0 and 16:1 (M=1185) and 16:0 and 18:1 (M=1203) respectively, as well as an acetyl residue (on the initial phosphate position). Although it was possible to assign the fatty acid substitution pattern to the two glycerol residue $Gro^I$ and $Gro^{II}$ by these analyses, the exact substitution pattern of the fatty acids could only be determined by NMR analysis (see below). Due to thermal instability of the molecules, the DIP MS analyses of the two intact phospholipid derivatives PL1 and PL2 could not be completely analyzed and were therefore further examined by means of MALDI-TOF-MS analysis.

4.1.2. MALDI-TOF-MS

MALDI-TOF-MS analyses were carried out on a Bruker Reflex II spectrometer in the reflector mode at an acceleration potential of 20 kV by means of the "delayed ion extraction" in the positive mode. The per-O-acetylated and phosphomethylated samples of PL1 and PL2 were re-suspended in chloroform (10 µml) and 2 µl solution thereof were mixed with 2 µl of a matrix solution (0.5 M 2,4,6-trihydroxyacetophenone; Aldrich, Steinheim). An aliquot of this mixture (0.5 µl) was applied to a metal support, dried with warm air and immediately thereafter placed into the spectrometer. Calibration of the spectra was performed using an internal standard (Angiotensin). All mass data apply exclusively to the monoisotopic mass of the molecules.

Figure 2:
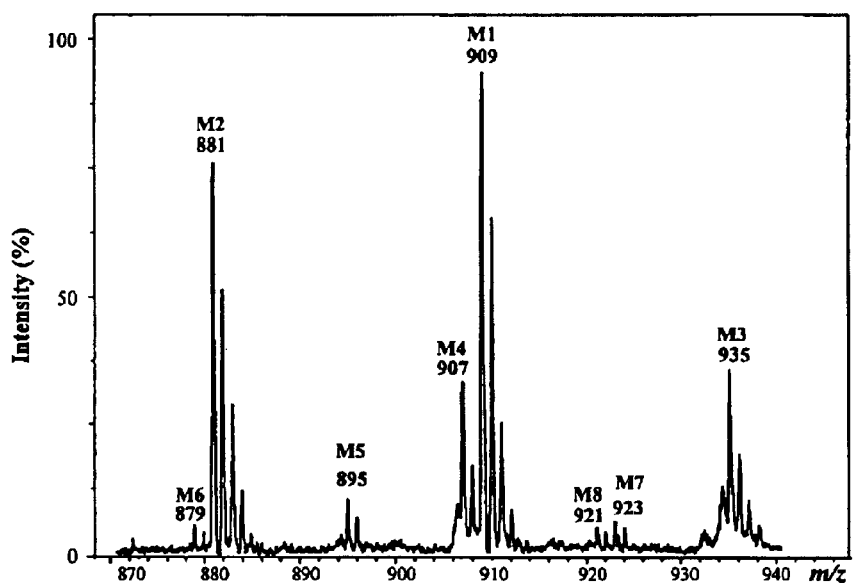
Figure 2:
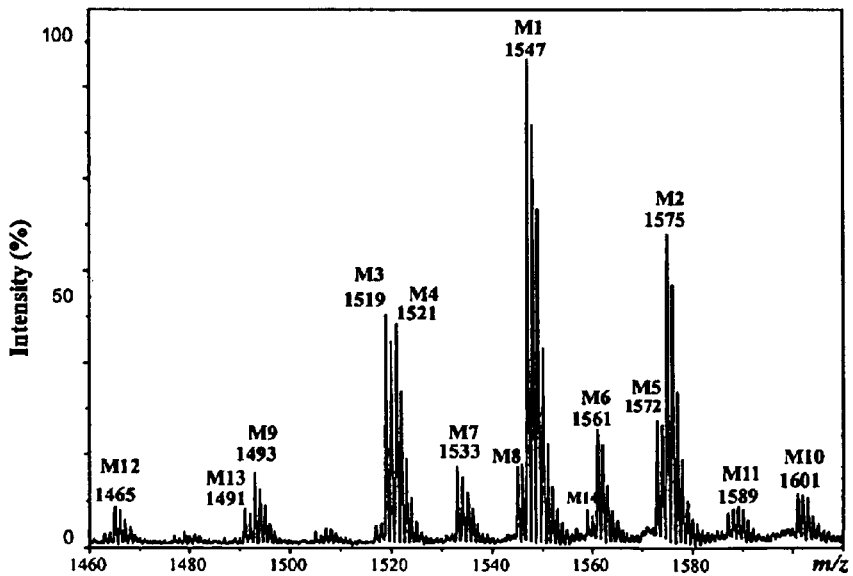

In each case, two derivatives of both phospholipids were analyzed by MALDI-TOF-MS: the free phosphoric acid derivatives and the phosphomethyl esters (PL1 and PL2, see FIG. 2). The free phosphoric acid derivative of PL1 showed prior to esterification of the phosphate residue (diazomethane) in the positive reflector mode a pseudomolecular ion $[M-H+Na]^+$ at m/z=1116,48, corresponding to the calculated formula $C_{54}H_{95}O_{20}P$ (M=1094,56). The non-esterified phosphoric acid derivative of PL2 showed under the same conditions a pseudomolecular ion $[M-H+Na]^+$ at m/z=1796,43, corresponding to the formula $C_{94}H_{167}O_{28}P$ (M=1775,06) and thus carrying in addition a hexose and a fatty acid (16:0 and/or 18:1) in comparison to PL1.

Note: The mass of the MALDI-TOF-MS analyses given herein in all cases only relate to the smallest monoisotopic pseudomolecule ion or mass fragment. That means, in all mass data only the smallest fatty acid (16:0) was considered (see FIG. 2). All pseudomolecular ions presented herein showed per fatty acid always a heterogeneity resulting from the exchange of 16:0, 16:1, 18:0 and 18:1, this heterogeneity influencing all mass spectra (DIP and MALDI), but is not considered in the mass data provided herein.

PL1 showed after treatment with diazomethane a pseudomolecular ion $[M-H+Na]^{30}$ at m/z=1130,69 which corresponds to the formula $C_{55}H_{97}O_{20}P$ (M=1108,57) and thus contains only one additional methyl group ($\Box$m/z=14) in comparison to the free acid. PL2 showed under the same conditions a pseudomolecular ion $[M-H+Na]^{30}$ at m/z=1811,42, which corresponds to the formula $C_{95}Hl_{69}O_{28}P$ (M=1789,07) and also contains only one additional methyl group ($\Box$m/z=14) in comparison with the free acid. Thus, not only the preceding MS analyses (DIP MS) were confirmed, but it was also unambiguously demonstrated that both PL1 and PL2 represent phosphodiesters, which are likely to be substituted with two glycerol residues. In both cases only one methyl group was introduced by a diazomethane treatment and transformation into the corresponding methyl ester.

4.2. Proton Nuclear Magnetic Spectroscopic Analysis ($^1$H-NMR)

The per-O-acetylated and purified samples (2–4, 30–200 µg) were dissolved in 100 µl CDCl$_3$ (99.96% Cambridge Isotope Laboratories, Andover, Mass., USA), and transferred into special capillary NMR microtubes (2.5 mm OD, Wilmad, Buena, N.J., U.S.A.). The proton spectra ($^1$H-NMR) were recorded on a 600 MHz Spectrometer (Bruker Avance DRX 600), equipped with a special microprobe head (PH TXI 600SB). The samples were measured at 300K with reference to internal trimethylsilane (TMS, $\delta_H$=0.000 ppm). One- and two-dimensional homonuclear spectra ($^1$H, $^1$H COSY, ROESY, and relayed COSY) were performed using standard Bruker software (XWINNMR, Version 1.3).

The one-dimensional (1D) $^1$H-NMR spectra (600 MHz, microprobe head) of the di-(2,≈200 µg), tri-(3≈200 µg), and tetrahexosyl diacylglycerolipids (4≈50 µg) of compounds 2, 3, and 4 are shown in FIGS. 3a–c and the results are set forth in Table 1 (Annex).

Assignment of the signals was carried out by 1D and two-dimensional (2D) proton nuclear magnetic resonance spectrometry ($^1$H, $^1$H COSY, relayed $^1$H, $^1$H COSY, ROESY) in comparison with the structurally related β-gentiobiose octaacetate (1) which served as a reference substance for unambiguous assignment and which is therefore also included in Table I. The β-anomeric configuration of all hexoses in the substance results from the coupling constants $J_{1,2}$ being between 7.6 and 8 Hz for all glucoses. The other coupling constants of the pyranosidic ring protons H-2, H-3, and H-4 and H-5 ($J_{2,3}$, $J_{3,4}$ $J_{4,5}$) were all larger than 9.5 Hz, indicating glucopyranose. The chemical shift of the methylene protons (H-6a and H-6b) as well as their coupling constants ($J_{6a,6b}$) in the terminal Glc residue (A) were found to be identical in all oligosaccharides (4.062±0.005 ppm for H-6a and 4.205±0.005 ppm for H-6b) as compared with those of H-6a,6b in residue A of the β-gentiobiose octaacetate, thus allowing the assignment of the spin systems of all terminal Glc residues A in the oligosaccbarides 2, 3, and 4 on the one hand, but also in PL1 and PL2.

The β(1→6)glycosidic bond could be determined by means of the shift towards a higher field of the (overlapping) signals of H-6a and H-6b in residues B, C and D (3.855±0.05 ppm) since these signals clearly differed from the non-substituted methylene signals of the terminal H-6a,6b (A). This fact clearly indicates that all Glc residues of the compounds 2, 3, and 4 are identically, i.e. β(1→6) glycosidically interlinked. This observation could be confirmed by means of a two-dimensional spectrum ($^1$H, $^1$H COSY, FIG. 4, bottom) and a nuclear Overhauser spectrum (rotating-frame NOE spectroscopy, ROESY, FIG. 4, above) of trisaccharide 3. A ROESY spectrum showed (indicated) cross-peaks of the anomeric H-1 protons H-1$^A$, H-1$^B$, and H-1$^C$ which could be observed between H-1$^A$/H-6a,6b$^B$, H-1$^B$/H-6a,6b$^C$, and H-1C/H-3a,3b$^{Gro}$ (FIG. 5), allowing an unambiguous assignment of the three spin systems to each of the glucosyl residues A, B and C.

Figure 3:
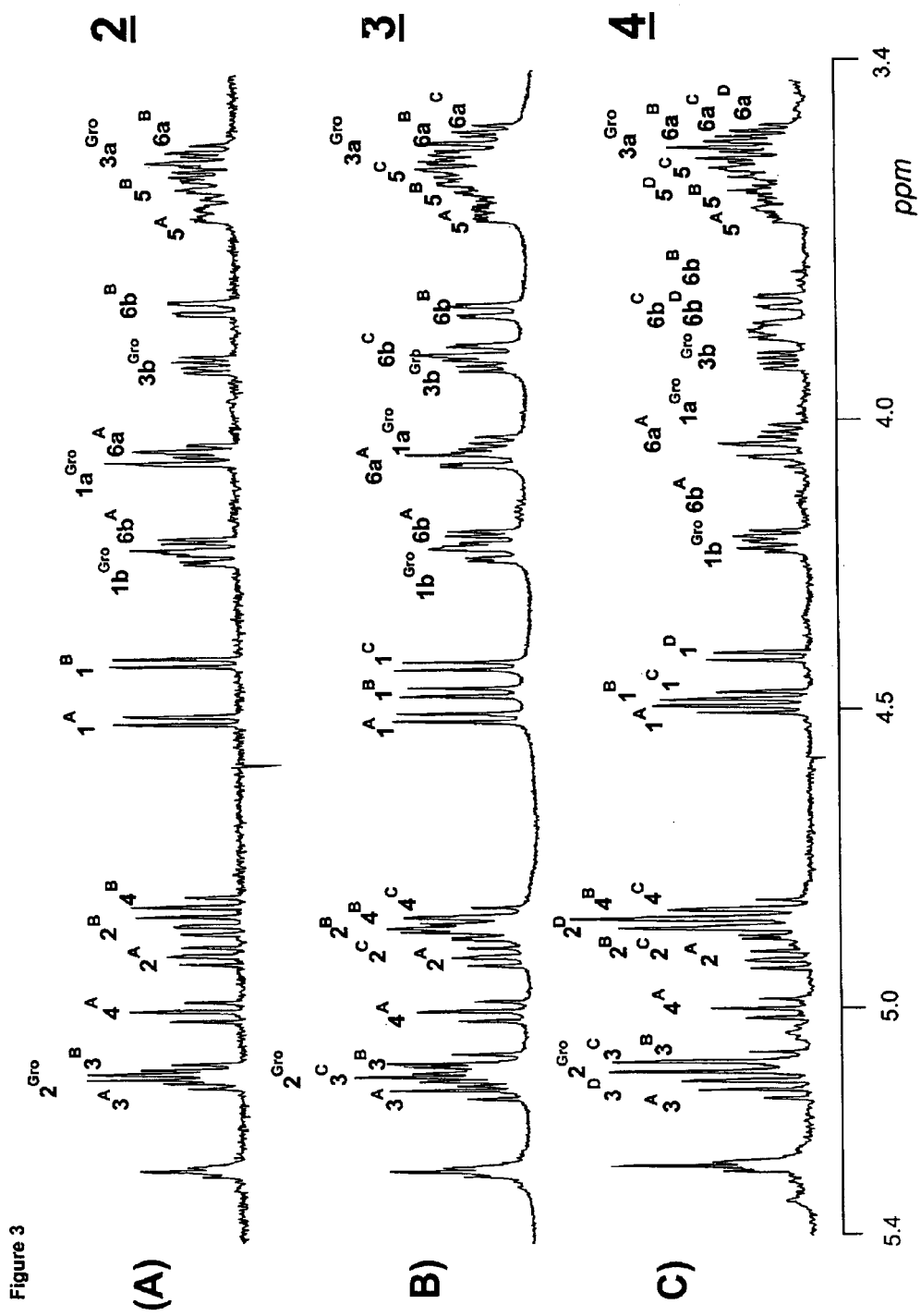

In addition to the glycosyl residues in all $^1$H-NMR spectra, signals of the glycerol moiety (H-1a, 1b$^{Gro}$, H-2$^{Gro}$, and H-3a,3b$^{Gro}$) could also be identified (FIG. 3, Table 1). The fatty acids showed the expected methylene (—CH$_2$—, 1.185 ppm) and methyl protons (—CH$_3$, 0.812 ppm). Finally, signals from olefinic protons (—CH=CH—, ≈5.27 ppm) could also be found in all glycolipids 2–4, PL1 and PL2, which from the MS spectra could be assigned to the unsaturated fatty acids 16:1 and/or 18:1.

In accordance with the non-phosphorylated compounds 1–4, NMR analyses were carried out only with the per-O-acetylated mono methyl ester derivatives Samples (0.1–0.2 mg) were dissolved in 500 µl CDCl$_3$ (99.96% Cambridge Isotope Laboratories, Andover, Mass., U.S.A.) and measured in 5 mm NMR tubes (Ultra Precision NMR sample tubes., Isocom, Landshut) at 300 K. Proton and Phosphorous-31 spectra ($^1$H- and $^{31}$P NMR) were recorded with a 600 MHz spectrometer (Bruker Avance DRX 600) equipped with an inverse probe head (5 mm TXI 13C), and the carbon 13 ($^{13}$C NMR) spectra were recorded with 360 MHz Bruker AM spectrometer (5 mm dual probe head) at 90,6 MHz. The chemical shift was measured with reference to internal tetramethylsilane (TMS, $\delta_H$=0.000 ppm) and chloroform (CHCl$_3$, $\delta_C$=77.00 ppm), respectively. $^{31}$P NMR spectra were recorded at 242.9 MHz and calibrated with reference to an external standard (85% $H_3PO_4$=0.0 ppm) One (1D) and two-dimensional (2D) homonuclear spectra ($^1H$, $^1H$ COSY, NOESY, and relayed COSY) and heteronuclear spectra [$^1H$, $^{13}C$ and $^1H$, $^{31}P$ HMQC (heteronuclear multiple quantum coherence) as well as $^1H$, $^{13}C$ HMBC (hetero multiple bond correlation)] were recorded with a standard Bruker software (XWINNMR, Version 1.3).

In the $^1H$-NMR spectrum (FIG. 6 and Table 2), PL1 showed, in accordance with MGlcD: {3-[O-β-D-glucopyranosyl]-1,2diacylglycerol }, characteristic signals corresponding to a β-glycosidically bonded Glc residue. Surprisingly, the anomeric proton H-1 was cleaved into a couple of signals (H-1 and H-1') with a similar intensity (H-1, 4.461 ppm, $J_{1,2}$ 7.9 Hz; H-1', 4.457 ppm, $J_{1,2}$ 7.9 Hz. While the other protons (H-2, H-3, H-4, H-5, H-6a,b) showed identical chemical shift and coupling constants as compared with MGlcD, the protons of H-3a$^{Gro\ I}$ and H-3b$^{Gro\ I}$ (3.62 and 3.88 ppm) on the one hand and H-1a$^{Gro\ II}$ and H-1b$^{Gro\ II}$ (4.11 and 4.31 ppm) on the other hand were split: fine resolution of the two other methylene proton signals of the glycerol residues I and II (H-1a,b$^{Gro\ I}$ and H-3a,b$^{Gro\ II}$; ~4.08–4.14 ppm) could, however, not be observed. Further, we observed two singular methine protons for H-2$^{Gro\ I}$ (ddd, 5.082 ppm, 5.3 Hz) and H-2$^{Gro\ II}$ (ddd, 5.168 ppm, 5.3 Hz) as to be expected for a diglyceride.

Further characteristic signals were of the methyl group of the phosphate ester, which also exhibited a characteristic split doublet (POC$\underline{H_3}$, 3.828 and 3.810 ppm) with a characteristic $J_{H,P}$ coupling of 11.2 Hz. A phosphate monomethylester, PL1 could be identified as a phosphodiester via the integral of the signal of the phosphomethyl group (3H). This confirmed the results of MS analyses. Finally, 5 OAc signals could be detected (2.026, 2.018, 1.989, 1.954, 1.934 ppm; all s), which led to the conclusion that, besides the four OAc groups of the terminal Glc residue, presumably a fifth OAc group was bound to one of the two glycerol residues. The accurate fatty acid distribution pattern could be partially determined using an HMBC experiment. A fatty acid in position sn-1 of glycerol residue II could be assigned via the connectivities of the α-methyl protons of the fatty acids (—O—COCH$_2$—). However, due to the small amount of substance, the substitution of the second fatty acid could not be determined in the HMBC experiment and could only be investigated based on MS analyses.

In $^{31}P$ NMR (FIG. 7 and Table 3), the phosphate signal of PL1 is split (0.514 and 0.444 ppm) and appears as a singlet in the decoupled spectrum. The $^1H$, $^{31}P$-HMQC experiment (i) showed the expected connectivity with the phosphomethyl ester group (3.828 and 3.810 ppm), and (ii) revealed two methylene protons of glycerol residue I (H-1a,b$^{Gro\ I}$ and H-3a,b$^{Gro\ II})(~$4.08–4.14 ppm) to which the phosphomethyl group is bound. Hence, the phosphate substitution could be determined. Thus, based on this experiment, the connection of glycerol residues I and II via a phosphate diester could be proven, which could already be assumed due the presence of phosphomonomethyl ester in NMR analysis and due to characteristic fragments in MS analysis.

The splitting of the signals of H-1$^{Glc}$, H-3$^{Gro\ I}$ and H-1a,b$^{Gro\ II}$ is especially notable. This anomaly in $^1H$ NMR can be explained by the presence of a pair of diastereomers of PL1. By introducing a methyl group, the prochiral phosphate (R—O—PO(OH)—OR') in the middle of the molecule becomes chiral (R—O—PO(OMe)—OR') which results in two diastereomeric phospholipids PL1 and PL1'. A corresponding chirality of the phosphorous atom was already observed and described for other phospholipids in $^1H$-, $^{13}C$ and $^{31}P$-NMR spectra (Bruzik et al., 1983).

Phospholipid 2 (PL2) showed the same characteristic splitting of two anomeric protons in $^1H$-NMR. In this case, the anomeric protons are of the two glucose residues Glc$^A$ and Glc$^B$ (H-1$^A$ and H-1$^{'A}$; 4.647 and 4.635 ppm, $J_{1,2}$ 7.7 Hz) and H-1$^B$ and H-1$^{'B}$ (4.533 and 4.524 ppm, $J_{1,2}$ 7.9 Hz). These splittings are characteristic for diastereomeric pairs analogous to PL1. Thus, a structural relationship of both phospholipids and, as a consequence, a correlation in the biosynthesis of these phospholipids can be assumed. The $^1H$-NMR spectrum of PL2 showed high similarity with the one of DGlcD (2) which made the interpretation of the NMR spectra and thus the structural analysis easier. By comparison of both $^1H$-NMR spectra, the substitution of the fourth acyl residue (16:0 or 18:1) in position C-6$^A$ of terminal glucose could be determined. (The third acyl residue is connected with the C2 group of Gro').

Further characteristic signals were of the phosphomethyl ester, which also exhibited a split doublet revealing the chirality of the phosphate residue, and thus the diastereomeric nature of the molecule (3.835 and 3.818 ppm, $J_{P,H}$ 11.2 Hz). In $^{31}P$-NMR, the phosphate signal of PL2 was also split (0.414 and 0.275 ppm) analogous to PL1, which is characteristic for the diastereomeric pair PL2 and PL2' (Bruzik et al., 1983).

Figure 9:
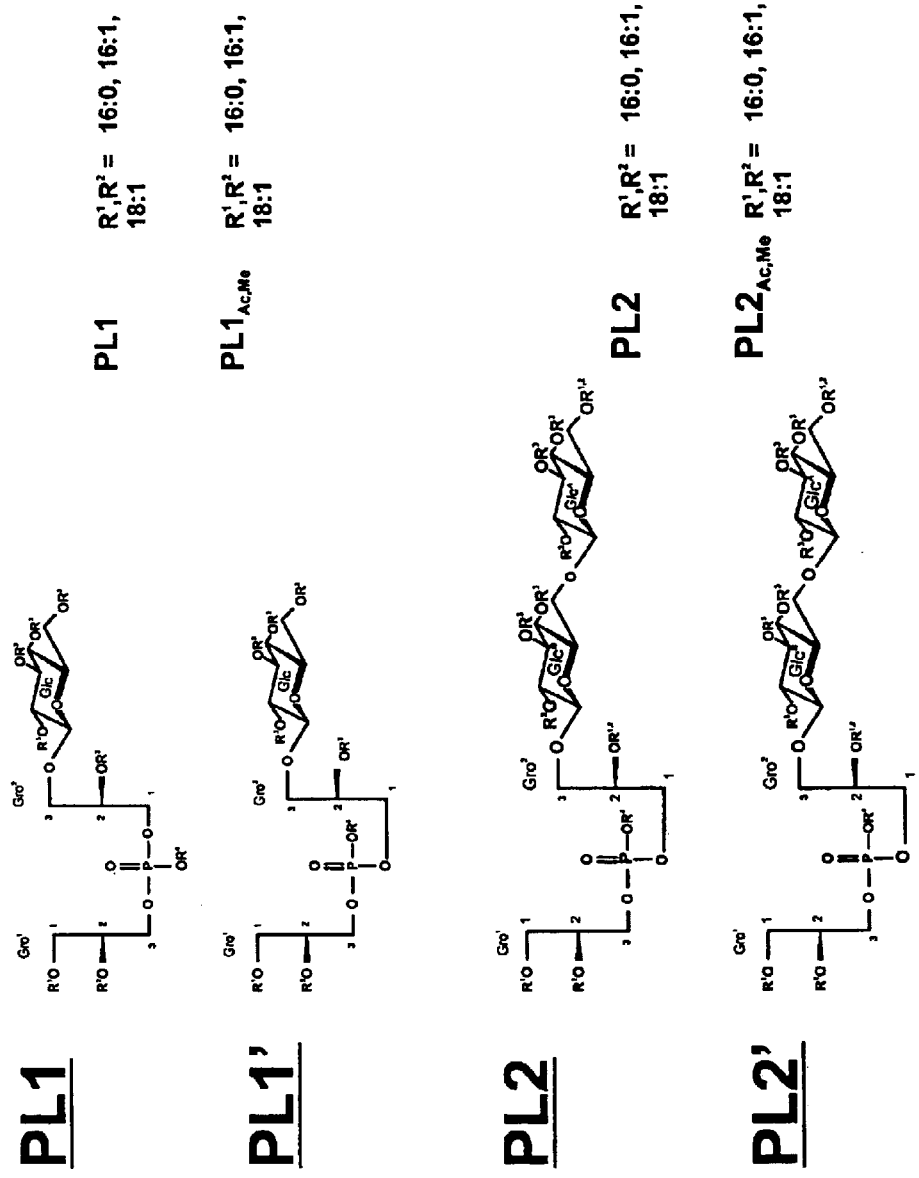

In conclusion, our MS (DIP and MALDI) and $^1H$-, $^{13}C$- and 31 P-NMR analyes unequivodcally identified three neutral and two inogenic glyolipids, which could be identified as di-, tri-, and tetrasaccharide-diacylglycerols 2, 3, and 4 with the following structure in the glycosyl moiety (FIG. 8):

β-D-Glcp-(1→6)-β-D-Glcp-(1→6)-Gro (2)(DGlcD),

β-D-Glcp-(1→6)-β-D-Glcp-(1→6)-β-D-Glcp-(1→6)-Gro (3)(TGlcD), and

β-D-Glcp-(1→6)-β-D-Glcp-(1→6)-β-D-Glcp-(1→6)-β-D-Glcp-(1→6)-Gro (4)(TeGlcD), as well as the phospholipid 1:3-[O-β-D-glucopyranosyl]-sn-glycerol-13'-phospho-1',2'-diacyl-sn-glycerol (PL1) and the phospholipid 2: {3-[O-(6'''-O-acyl)-β-D-glucopyranosyl-(1'''→6'')-O-β-D-glucopyranosyl]-2-acyl-sn-glycerol-1,3'-phospho-1'2'-diacyl-sn-glycerol} (PL2) (FIG. 9).

5. Enzyme Assay

Standard enzyme assays for determination of the activity of the processive glycosyl transferase were performed in a final volume of 100 μl, containing buffer 1, 20 μl E. coli BL21 (DE3) pEypfP24 and pEsay24 membrane fraction (20–40 μg of protein) and 250 000 dpm UDP-[$^{14}C$]-glucose (specific activity 10.8 GBq/mmol; 3.85 μM final concentration). The reaction was carried out for 1 h at 30° C. and stopped by the addition of chloroform/methanol (2:1; 2 ml). The organic mixture was washed with 0.7 ml of NaCl solution (0.45% (w/v)) and the resultant subphase recovered. An aliquot of the subphase was subjected to scintillation counting, and after removal of the solvent by evaporation with argon, the remaining part was used for separation by thin-layer chromatography.

Detergents such as octyl-β-D-glucopyranoside (Sigma), decyl-β-D-glucopyranoside (Sigma), SDS, Chaps (Signa), Tween 20, dodecyl-β-D-maltoside (Sigma) and sodium cholate (Sigma) were added in concentrations according to twice their critical micellar concentration (this applies only to the processive glycosyl transferase from B. subtilis ypfP).

Figure 10:
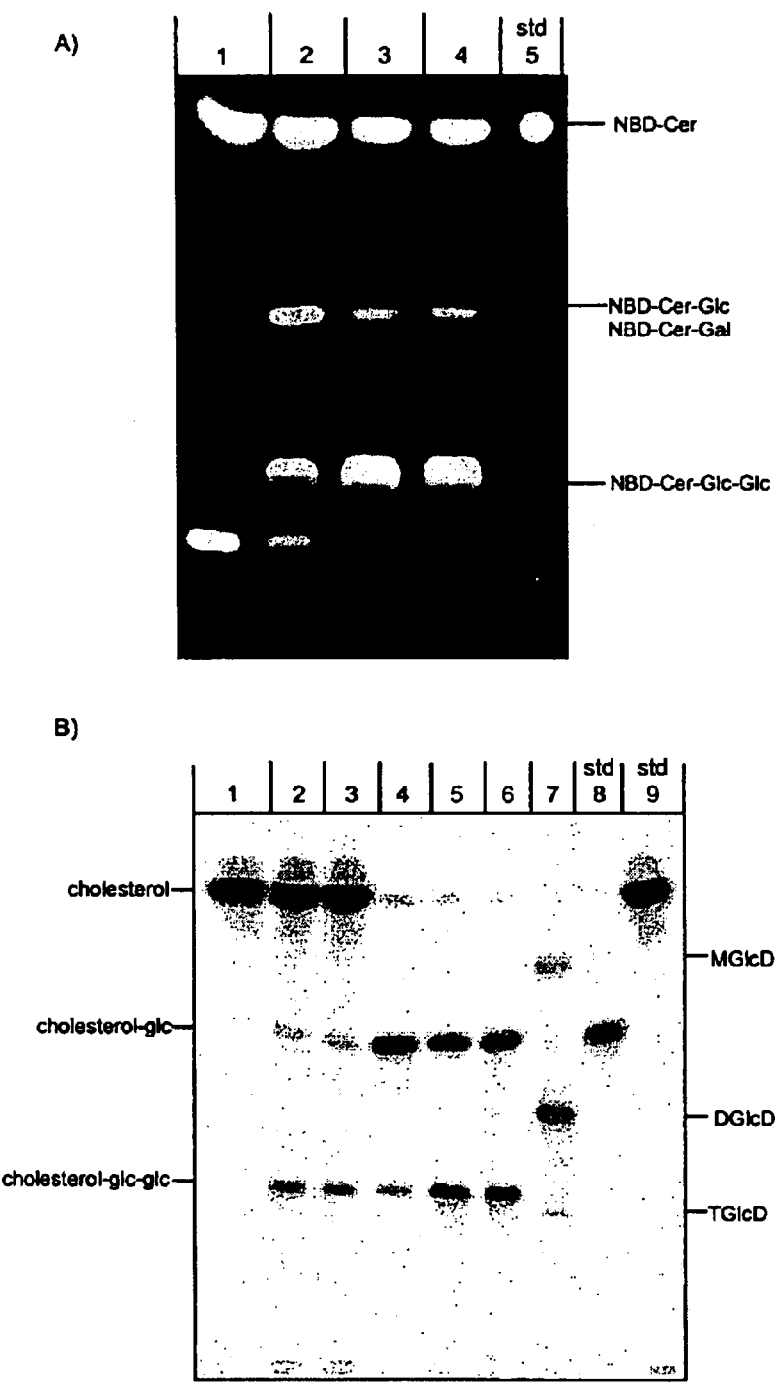

Ceramide was added as fluorescent D-erythro-C6-NBD-ceramide (Matreya, INC.), cholesterol was added as [4-$^{14}C$]cholesterol and steryl glucoside was added as $^{14}C$-labelled steryl glycoside (FIGS. 10/11). Radioactive products on thin-layer chromatography plates were detected by radio scanning (BAS-1000 Bio Imaging Analyzer, Fuji) (see FIG. 10).

Figure 11:
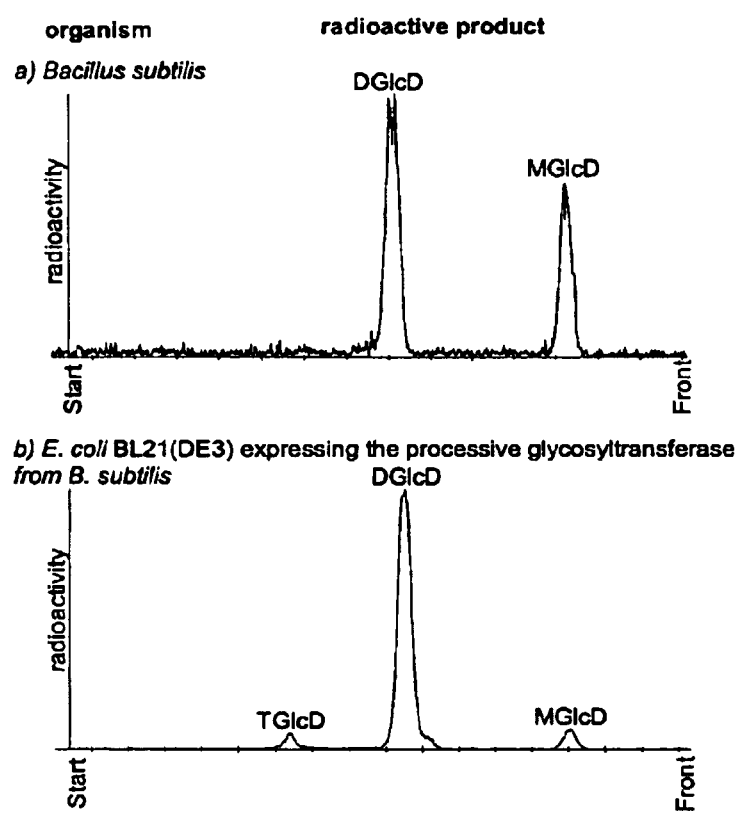

Assays with UDP-[$^{14}$C]glucose showed the highest incorporation of radioactivity with membrane fractions compared with the soluble and inclusion body fractions of *E. coli* BL21 (DE3) pEypfP24 and pEsay24. Therefore, all subsequent in vitro standard assays were carried out with membrane fractions and UDP-[$^{14}$C]glucose. The [$^{14}$C]-labeled lipophilic products counted for 70–80% of the label offered in the assay. Separation by TLC was used to identify lipophilic radioactive products, using a monogalactosyl diacylglycerol (MGD), DGlcD and TGlcD as non-radioactive standards. The highest proportion of radioactivity was found in DGlcD, whereas labeling of MGlcD and TGlcD (TeGlcD only for *B. subtilis*) was low (FIG. 11). Assays with membrane fractions of the untransformed *E. coli* did not show incorporation of radioactivity into lipophilic products. To increase the DAG concentration in the enzyme assay, the effects of several detergents on the enzymatic activity were tested. With the exception of lyso-PC (Sigma) and alkyl-β-D-glucopyranosides, the addition of all above-mentioned detergents resulted in complete inhibition of enzymatic activity. [$^{14}$C]-MGlcD and [$^{14}$C]-DGlcD from assays with transformed *E. coli* were isolated and subjected to various chemical and enzymatic treatments to identify their structure.

The DAG moiety in [$^{14}$C]DGlcD was confirmed by treatment with Rhizopus lipase. This lipase specifically releases the fatty acid from the sn 1-position of the DAG-containing lipid. As expected, the resulting radioactive product co-migrated with a lyso-DGlcD that had been prepared from non-radioactive DGlcD by the same treatment. Incubation of [$^{14}$C]DGlcD with sodium methylate resulted in the release of a free fatty acid methyl ester and [$^{14}$C] glucosyl diacylglycerol, the same products were produced when using non-radioactive DGlcD of known structure. Characterization of the linkage between the first glucose and the DAG was carried out by incubation of the labeled MGlcD with cerebrosidase. This enzyme is specific for the β-glucosidic linkage, but is relatively unspecific for the hydrophobic part of its substrate (Vandeijagt et al., 1994). The incubation of [$^{14}$C]glucose-labeled MGlcD with cerebrosidase resulted in the release of labeled glucose and unlabeled DAG. The success of the hydrolysis was measured by scintillation counting of the aqueous and organic phase after phase partitioning. 90% of the label was found in the aqueous phase as compared with 15% in ski the control experiment, in which 85% of the radioactivity was recovered as [$^{14}$C]MGlcD in the organic phase. These results support the assumption of a β-glucosidic linkage between the first glucose and DAG in MGlcD.

6. Characterization of Glycosyltransferase Activity

The formation of three different radioactive products in the in vitro enzyme assay raises the question whether all of these products are produced by a single enzyme coded by ypfP genes. To answer this question, three of the possible sugar acceptors were incubated separately in labeled form with unlabeled UDP-glucose in the presence of the membrane fraction. The sugar acceptors were isolated from previous assays. Assays with radioactive [$^{14}$C]DAG [$^{14}$C]MGlcD and [$^{14}$C]DGlcD were performed by sonification of the radioactive substrates in 0.5 mN lyso-phosphatidylcholine (for [$^{14}$C]DAG) or in ethanol before adding the membrane fraction, buffer I and UDP-glucose (3.6 mM final concentration). The maximum ethanol concentration in assays was 5% (v/v). After conversion of the substrates, the lipophilic products were separated by TLC and detected by radio scanning (FIG. 12). [$^{14}$C]DAG was converted to [$^{14}$C]DGlcD and [$^{14}$C]TGlcD, [$^{14}$C]MGlcD to [$^{14}$C]DGlcD and [$^{14}$C]TGlcD an [$^{14}$C]DGlcD to [$^{14}$C]TGlcD. Conversion of radioactive labeled DGlcD to TGlcD did not occur any more with the *S. aureus* enzyme. Control experiments using the same substrates and untransformed *E. coli* membrane fractions did not result in any of the mentioned products. The results suggest processivity of the enzyme, whereby the starting reaction can be described as a UDP-glucose: 1,2-diacylglycerol-3-β-D-glycosyltransferase reaction. In subsequent reaction steps, however, the glucose acceptors vary and represent the products of previous additions of β-glucosyl residues.

To exclude a reaction mechanism based on the transfer of glycosyl residues from glycosides to various acceptors, as observed for glycosidases, the enzyme assay was carried out in the presence of a radioactively labeled MGlcD, but in the absence of UDP-glucose. No conversion of a radioactively labeled MGlcD could be observed. Incubation of YpfP with the glucosidase inhibitor deoxynoijrimycin (Alexis Deutschland GmbH) and substance 3 (provided by Dr. Y. Ichikawa) was perforrned as described by Ichikawa and Igaiashi, 1995. These compounds interfere with the transfer of glucose in reactions catalyzed by glucosylhydrolases, but not with the transfer of a sugarnucleotide-dcpendent glucosyltransferases. None of the inhibitors was able to inhibit the enzyme reaction. Both approaches suggest a transfer of glucose by a sugar nucleotide-dependent reaction. On the other hand, ricinoleic acid and oleic acid were able to inhibit the enzyme, inhibition varying with the concentration in the assay. Additions between 25 and 50 µg in 100 µl assay volume resulted in inhibition of DGlcD and TGlcD formation, the second and third step of the enzyme reaction. In these experiments, MGlcD accumulated in the assay, whereas MGlcD accumulated in normal assays in a low amount. Concentrations above 50 µg in the assay led to a complete inhibition of the enzyme. Hydrolysis experiments with sodium methylate excluded the possibility that ricinoleic acid (=12-D-hydroxy-oleic acid) was glucosylated.

7. Substrate Specificity

Substrate specificity was characterized regarding the sugar donor and the sugar acceptor. Apart from UDP-[$^{14}$C]glucose, UDP-[$^{14}$C]galactose was also tested, but galactose was not incorporated into lipophilic products. Experiments concerning the sugar acceptor showed that besides DAG, MGlcD and DGlcD also alkyl-β-D-glucopyranosides can serve as acceptor (this applies only for the *B. subtilis* enzyme). This resulted in products, which tentatively have been identified as alkyl diglucosides. However, the only evidence available so far are the Rf-values of the resulting products and their stability towards alkaline hydrolysis. Neither alkyl-α-D-glucopyranoside nor alkyl-β-D-glucopyranoside could serve as acceptor. The *S. aureus* enzyme could convert sterol, as well as steryl glucoside (FIG. 10). This data shows that the YpfP enzymes are less specific concerning the sugar acceptor, but have a higher specificity for the sugar donor UDP-glucose.

General Cloning and Transformation Techniques

The recombinant DNA molecules according to the invention can be produced by standard techniques, as, for example, described in the Laboratory Manual by Sambrook et al., vide supra. Also, production of transgenic cells and organisms can be performed using conventional transformation methods, well-known in the art. This applies to microorganisms and yeast, as well as to plants. For introducing DNA into a plant host cell several techniques are available and the person skilled in the art can easily choose a suitable transformation procedure. These techniques comprise the transformation of plant cells with T-DNA using *Aerobacterium tumefaciens* or *Agrobacterium rhizozenes* as transformation means, fusion of protoplasts, direct gene transfer of isolated DNA into protoplasts, microinjection or electroporation of DNA, introducing DNA via biolistic methods and other procedures. In an alternative embodiment of the invention the nucleic acid molecules of the invention can be introduced into plant cells via viral infection. These techniques are all described in the literature, as are suitable binary vectors and expression vectors.

For constructing the recombinant nucleic acid molecules according to the invention, the skilled person can use any DNA sequence that codes for a protein having the biological activity of a processive diacylglycerol glycosyltransferase, including DNA sequences which hybridize with the DNA sequences disclosed herein. In the context of the invention, the term "hybridization" means a hybridization under convential conditions, preferably under stringent conditions, as e.g. described in Sambrook et al. (1989), Molecular Cloning: A Laboratory Manual, 2nd edition, Cold Spring Harbor Laboratory Press, Cold Spring Harbor, N.Y. Nucleic acid molecules that hybridize with the molecules of the invention may isolated e.g. from genomic or cDNA libraries. Identification and isolation of such nucleic molecules can be carried out using the nucleic acid molecules of the invention or fragments or reverse complements thereof, e.g. by hybridization under standard conditions (Sambrook et al., supra). For instance, nucleic acid molecules which display exactly or essentially the nucleic acid sequences of the invention or portions thereof can be used as hybridization probes. Also synthetic fragments, which are synthesized using common synthesis processes and which correspond basically to one of the DNA sequences or nucleic acid molecules of the invention can be used as hybridization probes. When genes are identified and isolated, which hybridize to the DNA sequences of the invention, it is necessary to determine their sequence and the sequence and characteristics of the proteins encoded by them. The man skilled in the art has a variety of biochemical, biotechnological and genetic engineering methods for the characterization of the nucleic acid molecules and the proteins at his disposal. The molecules that hybridize to the nucleic acid molecules of the invention comprise also fragments and (degenerated or allelic) derivatives of the nucleic acid molecules described herein. The terms "derivatives" means in this context that the sequences of such molecules differ from the molecules of the invention (as herein described) in one or more positions and show a high degree of homology to the sequences provides by the invention. Homology means an identity in sequence of at least 40%, in particular of at least 60%,preferably of more than 80% and more preferably of more than 90%. The deviations from the sequences of the invention may be generated by deletion, addition, substitution, insertion or recombination.

| Abbreviations | |
|---|---|
| AA | Amino acid |
| DAG | Diacylglycerol |
| DGlcD | Diglucosyl diacylglycerol |
| DHexD | Dihexosyl diacylglycerol |
| DNA | Deoxyribonucleic acid |
| Glc | Glucose |
| MGD | Monogalactosyl diacylglycerol |
| MGlcD | Monoglucosyl diacylglycerol |
| MHexD | Monohexosyl diacylglycerol |

| -continued | |
|---|---|
| Abbreviations | |
| PAGE | Polyacrylamide gel electrophoresis |
| PG | Phosphatidylglycerol |
| SDS | Sodium dodecyl sulfate |
| TeGlcD | Tetraglucosyl diacylglycerol |
| TGlcD | Triglucosyl diacylglycerol |
| THexD | Trihexosyl diacylglycerol |
| TeHexD | Tetrahexosyl diacylglycerol |
| PL1 | Phospholipid 1 |
| PL2 | Phospholipid 2 |

Nucleotide Sequence

*B. subtilis* ypfp (SEQ ID NO. 1)

ttgaatacca ataaaagagt attaattttg actgcaaatt acggaaatgg acatgtgcag gtagccaaaa cactttatga acaatgtgta cggctcggct ttcagcatgt aacagtttct aatttgtacc aagagtcaaa tccgattgtt tcagaggtaa ctcaatacct ttatttaaaa agcttctcaa tcgggaaaca gttttatcgt ttgtmatt acggagttga caaaatctat aataaacgta aattcaatat ttactttaaa atgggtaata aaagattggg cgaacttgtc gatgaacatc agcccgatat tattattaat acatttccga tgatcgtcgt gccggaatac agacgccgaa ctggaagagt cattcctacc ttcaacgtta tgactgatt ttgtcttcat aaaatttggg ttcacgaaaa cgtggataaa tattatgtgg cgacagatta cgtgaaggaa aaactgctgg agatcggcac tcatccaagc aatgaaaa tcacaggaat tccaatcagg ccgcaatttg aagaatccat gcctgttggc ccgatatata aaaagtacaa tcttccacca aacaaaaaag tgcttctgat catggcaggt gctcacggtg tattaaagaa cgtaaaagag ctgtgcgaaa accttgtcaa ggatgaccaa gtgcaagtag ttgtcgtgtg cgggaaaat acggctttaa aagaatcttt gagtgcgctt gaagcggaaa atggtgacaa attaaaagtt ctgggctatg tggagcgcat tgatgagcta tttcggatca cagattgcat gattaccaag cccggcggca ttactttgac agaagccaca gccattggag tgcctgtcat tctgtacaaa cccgtgcctg gccaggaaaa agaaaatgca aacuctttg aagaccgcgg agctgccatc gttgtgaacc gtcatgaaga gattctcgag tcagtcactt ccctcttgc agatgaagat accttgcatc gcatgaagaa aaacattaag gaccttcatt tagcaaactc ctctgaagtg attttagagg atatcctgaa ggaatcagaa atgatgaccg ccaaacaaaa agccaaagtg ctatcgtaa

*S. aureus* ypfP (SEQ ID NO. 3)

Atggttactca aaataaaaag atattgatta ttactggctc attcggtaac ggtcatatgc aagttacaca gagtatcgtt aatcaactta atgatatgaa tctagaccat ttaagcgtcattgagcacga tttatttatg gaagctcatc caattttgac ttctatttgt aaaaaatggt atatcaatag ctttaaatat tttagaaata tgtacaaagg gttttatac agccgcccag ataaactaga caaatgtttt tacaaatact atggacttaa taagttaatt aatttattgataaaagaaaa gccagattta atattattaa cgtttcctac accagttatg tcggtactaa ctgagcaatt taacattaat attccagttg ctacagtgat gacagactat cgcttacata aaaactggat tacgccgtat tcaacaagat attatgtggc aacaaaagaa acgaaacaag acttcataga cgtaggtatt gatccttcaa cagttaaagt gacaggtatt cctatgata acaaatttga aacgcctatt aatcaaaagc agtggttaat agacaacaac ttagatccag ataagcaaac tattttaatg tcagctggtg catttggtgt atctaaaggt tttgacacga tgattactga tatattagcg aaaagtgcaa atgcacaagt agttatgatt tgtggtaaga gcaaagagct aaagcgttct ttaacagcta agtaaatt aacgagaatg tatttgattc taggttatac caaacacatg aatgaatgga tggcatcaag tcaacttatg attacgaaac ctggtgggtat cacaataact gaaggtttcg cccgttgtat tccaatgatt ttcctaaatc ctgcacctgg tcaagagctt gaaaatgcct tttactttga agaaaggt tttggtaaaa cgctgatac tccag Amino Acid Sequence

*B.subtilis* YpfP (SEQ ID NO. 2) MNTNKRVLIL TANYGNGHVQ VAKTLYEQCV RLGFQHVTVS NLYQESNPIV SEVTQYLYLK SFSIGKQFYR LFYYGVDKIY NKRKFNIYFK MGNKRLGELV DEHQPDIIIN TFPMIVVPEY RRRTGRVIPT FNVMTDF-CLH KIWVHENVDK YYVATDYVK EKLLEIGTHPS NVKITGIPIR PQFEESMPVG PIYKKYNLSP NKKV-LLIMAG AHGVLKNVKE LCENLVKDDQ VQV-VVVCGKN TALKESLSAL EAENGDKLKV LGYVER-IDEL FRITDCMITK PGGITLTEAT AIGVPVILYK PVPGQEKENA NFFEDRGAAI VVNRHEEILE SVTSLLADED TLHRMKKNIK DLHLANSSEV ILEDILKESE MMTAKQKAKV LS S. aureus YpfP (SEQ ID NO. 4) MVTQNKKILI ITGSFGNGHM QVTQSIVNQL NDMNLDHLSV IEHDLFMEAH PILTSICKKW YINSFKYFRN MYKGFYYSRP DKLDKCFYKY YGLNKLINLL IKEKPDLILL TFPTPVMSVL TEQFNINIPV ATVMTDYRLH KNWITPYSTR YYVATKETKQ DFIDVGIDPS TVKVTGIPID NKFETPINQK QWLIDNNLDP DKQTILMSAG AFGVSKGFDT MITDILAKSA NAQVVMICGK SKELKRSLTA KFKLTRMYLI LGYTKHMNEW MASSQLMITK PGGITITEGF ARCIPMJFLN PAPGQELENA FYFEEKGFGK IADTPEEAIK IVASLTNGNE QLTNMISTME QDKIKYATQT ICRDLLDLIG HSSQPQEIYG KVPLYARFFV K

FIGURES

FIG. 1. Expression of the bacterial processive glycosyltransferases results in the biosynthesis of glycolipids in *E. coli* transformants. Lipid extracts were separated by TLC in chloroform: methanol: $H_2O$ (70:30:4). Total lipids were detected with ANS under UV and marked with pencil, glycolipids were detected with α-naphthol/$H_2SO_4$ and tentatively identified by co-chromatography with standards.

lane 1: *E. coli* BL21 (DE3), control lane 2: *E. coil* BL21 (DE3) pEypfP24, expressing the *B. subtilis* gene lane 3: *B. subtilis* lipid extract lane 4: *E. coil* BL2 1 (DE3) pEsay24, expressing the *S. aureus* gene lane 5: standards, MGD, DGlcD and TGlcD FIG. 2. Negative ion mode MALDI-RE-TOF mass spectra of PL1 (top) and PL2 (bottom). The dominating molecular species of PL1 (top, [M–H]+ at m/z=909) contains palmitic (16:0) and vaccenic acid (18:) residues, whereas the prevaling species of PL2 (bottom, [M–H]+ at m/z=1541) contains two palmitic (16:0) one palmitoleic (16:1) and one steraic acid (18:0) residue. The other species are described in the text.

FIG. 3(A,B,C). Partial $^1$H-NMR spectra (600 MHz, $CDCl_3$, 300K) of per-O-acetylated di-(2), tri-(3), and tetraglucosyl diacylglycerol (4).

Figure 4:
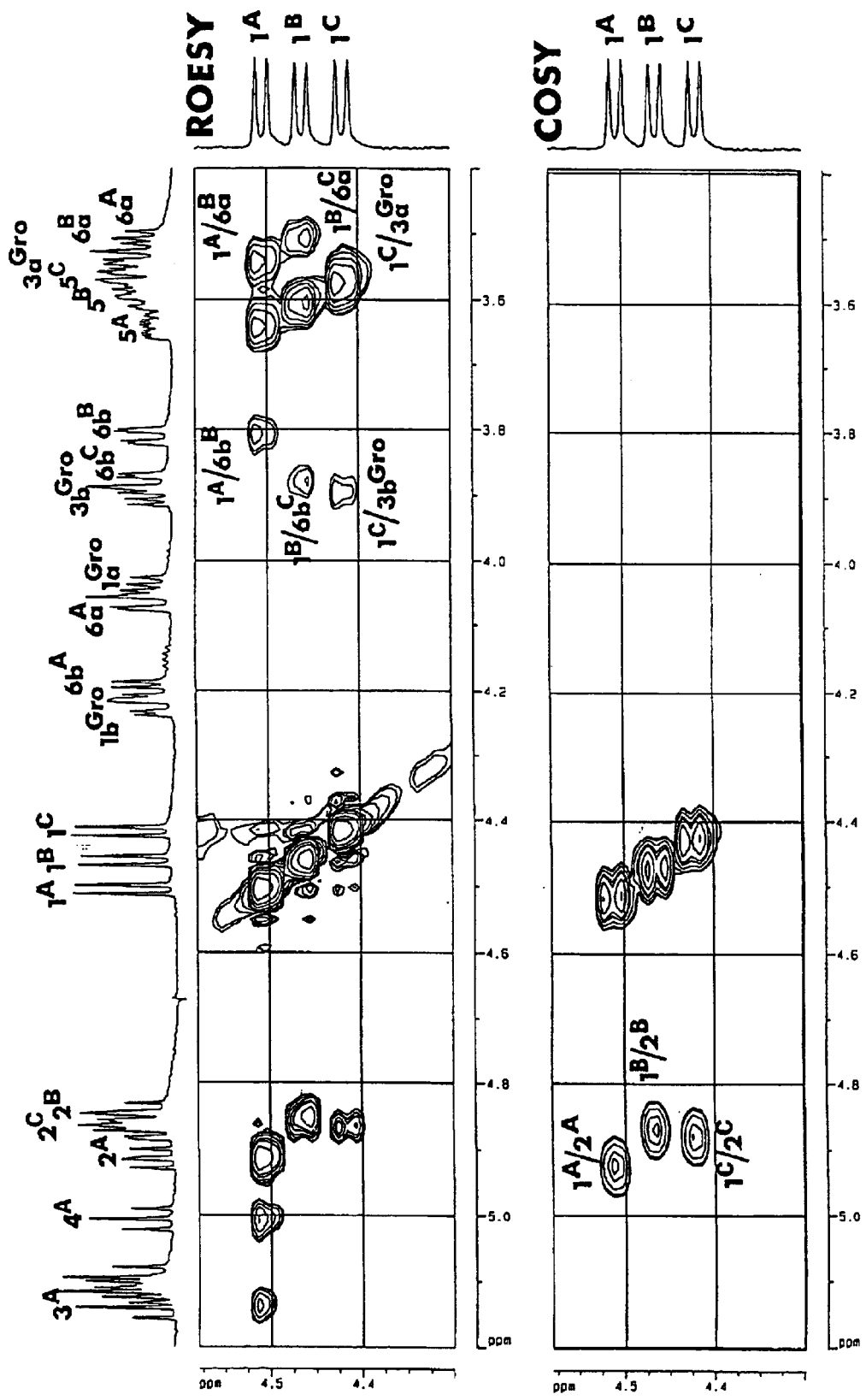

FIG. 4. Part of a 2D ROESY (upper) and 2D COSY (lower) spectrum (600 MHz, $CDCl_3$, 300K) of per O-acetylated triglucosyl diacylglycerol 3. NOE cross peaks used to assign the inter-residual connectivities are indicated in the ROESY spectrum as well as cross-peaks in the COSY spectrum. The corresponding parts of the 1D $^1$H-NMR spectrum are displayed along the axes.

Figure 5:
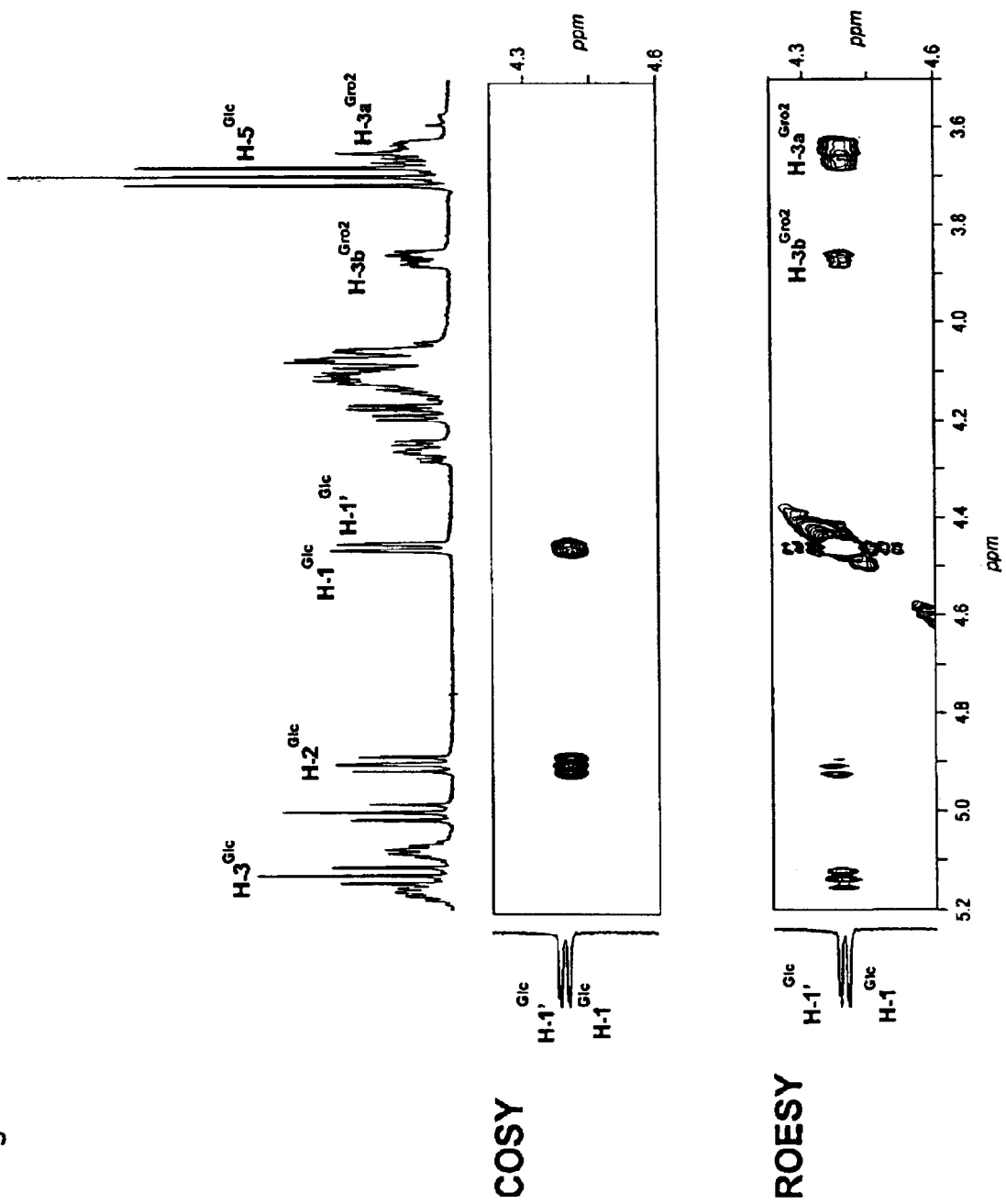

FIG. 5. Part of 2D ROESY (bottom) and 2D COSY(top) spectra (600 MHz, $CDCl_3$, 300K) of $PL1_{Ac,Me}$. The corresponding parts of the 1D $^1$H-NMR spectrum are displayed along the axes. The ROESY spectrum shows the connectivity between the anomeric proton H-$1^A$ of $Glc^A$ and the methylene protons H-$3a^{Gro2}$ and H-$3b^{Gro2}$. A mixing time of 250 ms was used in the ROESY experiment.

Figure 6:
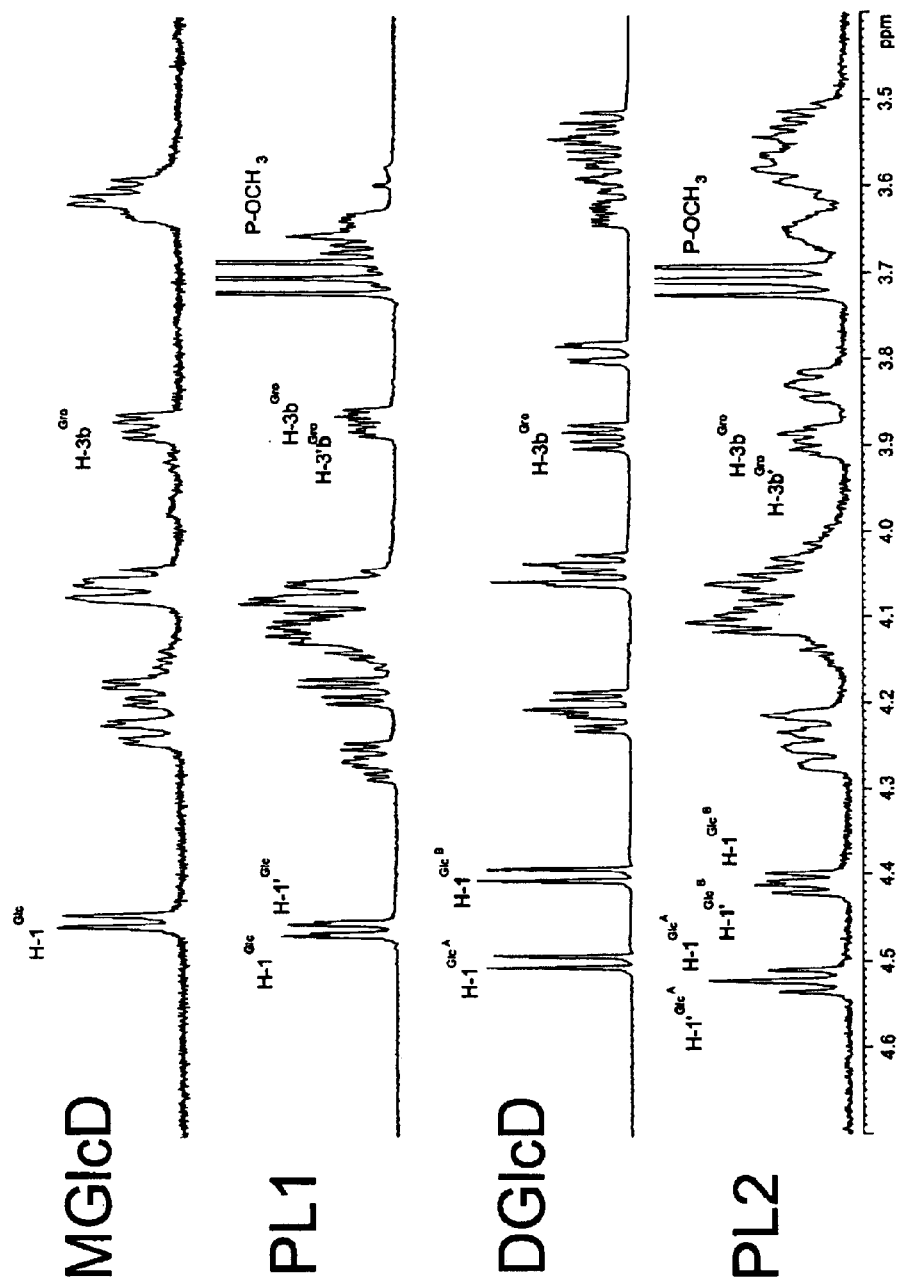

FIG. 6. Part of a $^1$H-NMR spectrum (600 MHz, $CDCl_3$, 300K) of $MGlcD_{Ac}$(a), $PL1_{Ac,Me}$(b) $DGlcD_{Ac}$(c), and $PL2_{Ac,Me}$(d). Only those signals are indicated which are split due to the chirality in the phosphate group when compairing a/b and c/d. Despite their distance to the phosphate group a paticularly large effect is seen for the anomeric protons of the disaccharide moeity of PL2. Spectra were apodized by Gaussian multiplication with LB-1.5 and GB 0.2 prior to Fourier transformation.

Figure 7:
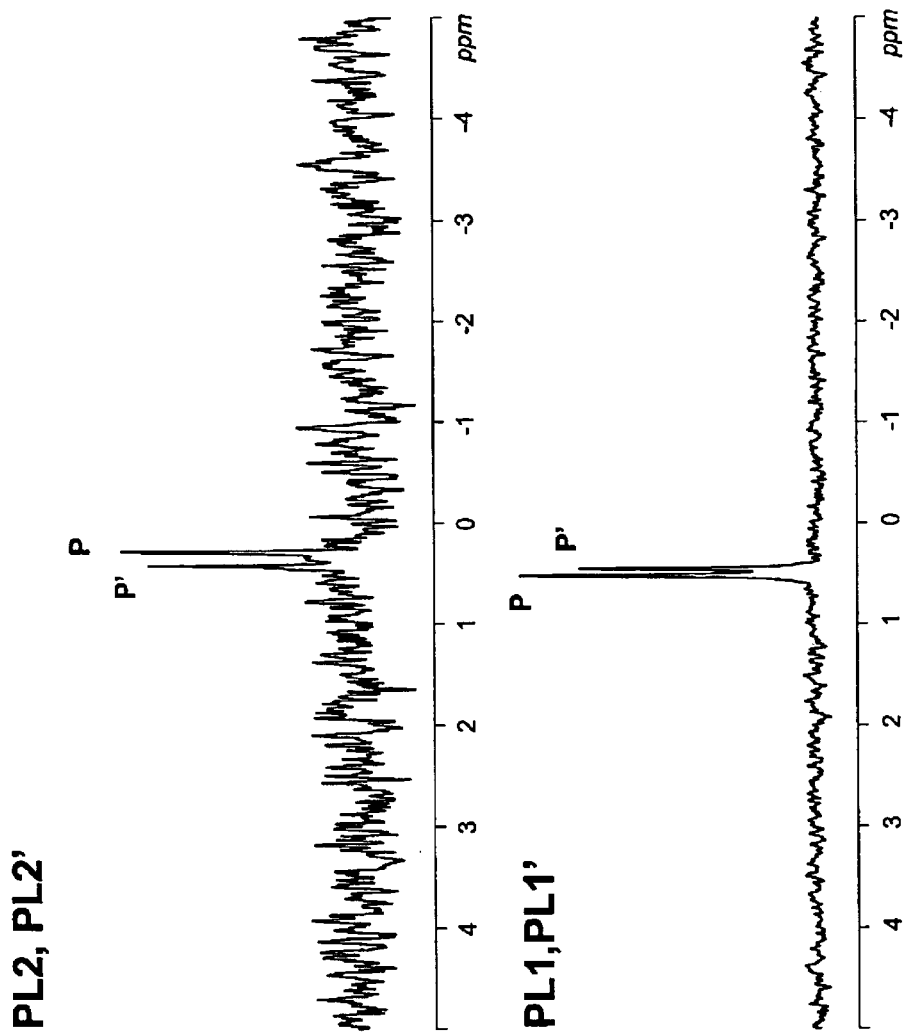

FIG. 7. Proton-decoupled $^{31}$P-NMR spectra (242.9 MHz, $CDCl_3$, 300K) of $PL1_{Ac,Me}$ and $PL2_{Ac,Me}$. Two different phosphate resonances for each pair of diastereomeric phospholipids (P, P') of PL1 (top) and PL2 (botom) are indicative of the chiral phosphate group in both phospholipids.

Figure 8:
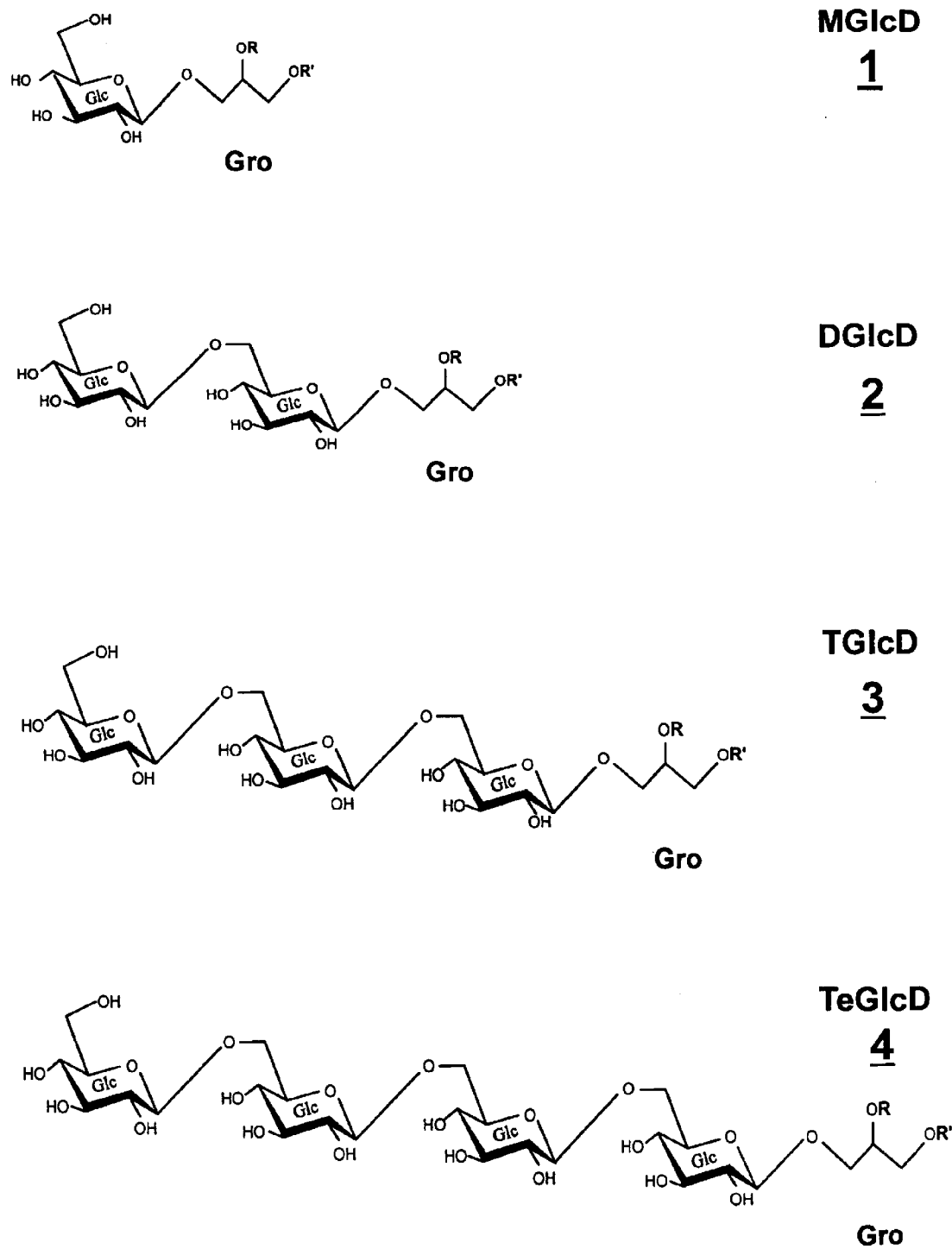

FIG. 8. Structures of MGlcD, DGlcD, TGlcD, TeGlcD. The numbers underlined are related to the numbers in the text.

FIG. 9: Structures of the two diasteriomeric forms of $PL1_{Ac,Me}$ and $PL2_{Ac,Me}$. The chirality in the phosphate group resulted from the transformation of $PL1_{Ac}$ and $PL2_{Ac}$ to their methyl phosphates.

FIG. 10. In vitro determination of acceptor specificities of bacterial processive glycosyltransferase from *S. aureus*.

Membrane fractions of *E. coli* BL21 (DE3) pEsay24 were used for in vitro enzyme assays with different labeled substrates as described in the experimental section. The lipophilic reaction products were subjected to thin-layer chromatography with subsequent radioscanning or fluorescence-detection for NBD-labelled products.

A) Enzyme assays with NBD-ceramide (NBD-Cer) as acceptor lane 1: *E. coli* BL21 (DE3) control lane 2–4: independent *E. coli* BL21 (DE3) pEscay24 lane 5: NBD-ceramide-standard

The product of highest polarity present in lane 1–4 is a degradation product of NBD-ceramide.

B) Enzyme assays with radiolabeled sugar donors or different radiolabeled lipophilic acceptors and cell-free extracts of *E. coli* BL21 (DE3) pEsay24(lane 1–7).

lane 1–3: +[$^{14}$C]cholesterol lane 4–6: +[$^{14}$C]cholesterolglucoside lane 7: +UDP-[$^{14}$C]glucose lane 8: standard, [$^{14}$C]cholesterolglucoside lane 9: standard [$^{14}$C]cholesterol The labelled product with higher polarity in lane 10 was also present in *E. coli* cells transformed with pUC18 and is therefore not resulting from processive glycosyltransferase activity. The structural assignments are tentative and based on chromatographic behaviour.

FIG. 11. In vitro demonstration of glucosyltransferase processivity of the glycosyltransferases from *B. subtilis* and *S. aureus* expressed in *E. coli* BL21 (DE). Cell extracts of *B. subtilis* and *E. coli* BL21 (DE3) expressing processive glycosyltransferase from *B. subtilis* and *S. aureus* were used for in vitro enzyme assays with UDP-[$^{14}$C]-glucose. Internal DAG served as sugar acceptor. The lipophilic reaction products were subjected to thin-layer chromatography with subsequent radioscanning. The products were identified by co-chromatography with unlabeled standards.

Figure 12:
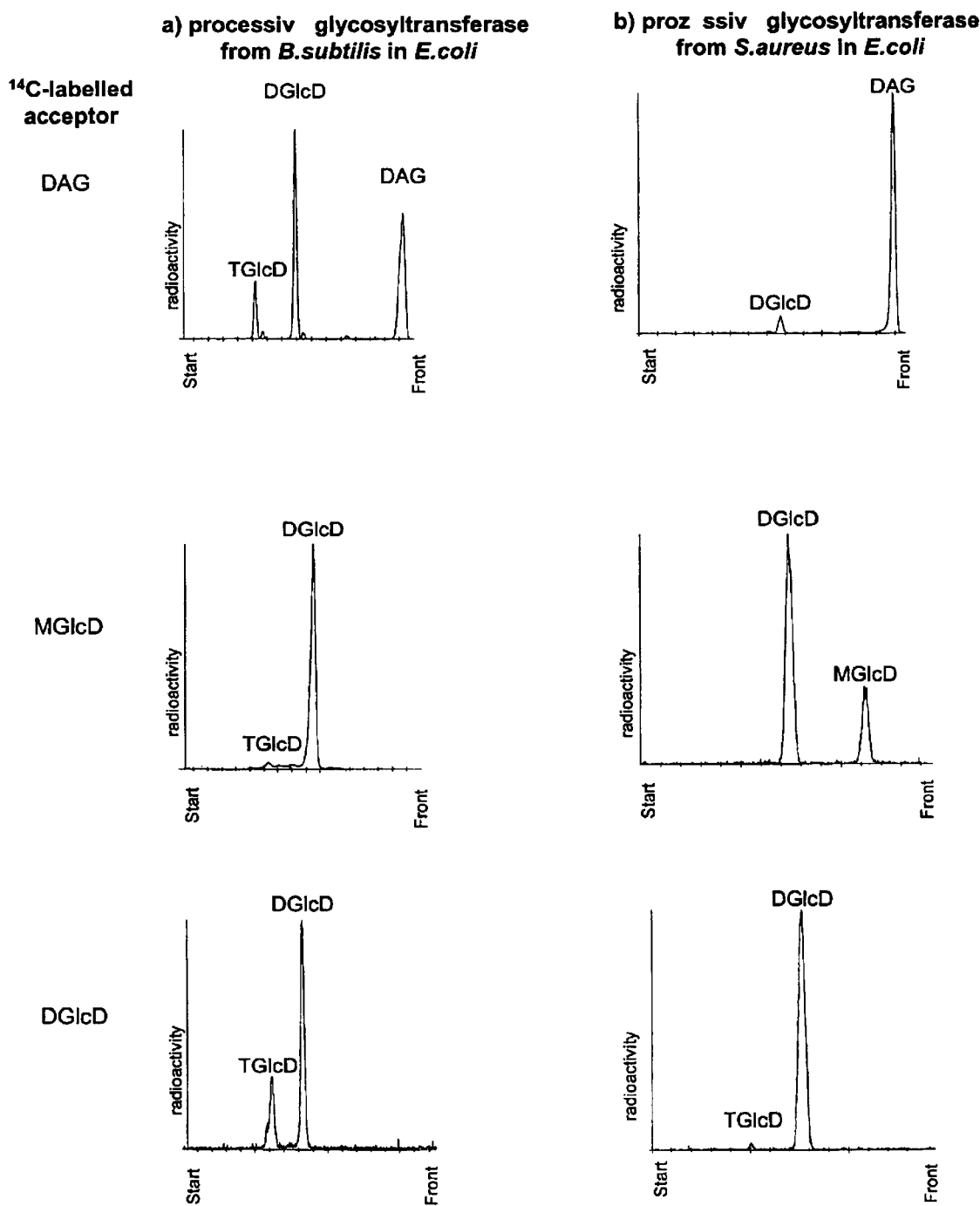

FIG. 12. In vitro demonstration of glucosyltransferase processivity of the glycosyltransferases from *B. subtilis* and *S. aureus* expressed in *E. coli* BL21 (DE). Membrane fractions of *E. coli* BL21 (DE3) expressing processive glycosyltransferase from *B. subtilis* and *S. aureus* were used for in vitro enzyme assays with unlabeled UDP-glucose and different radiolabeled acceptors as described in the experimental section. The lipophilic reaction products were subjected to thin-layer chromatography with subsequent radioscanning. The products were identified by co-chromatography with unlabeled standards.

REFERENCES

Altschul, S F., Gish, W., Miller, W., Myers, E. W., and Lipman, D. (1990) Basic local alignment search tool. J. Mol. Biol. 215: 403–410

Bruzik, K., R.-T. Jiang, and M. D. Tsai, (1983) Phospholipids Chiral at Phosphorus. Preparation and Spectral Properties of Chiral Thiophospholipids. *Biochemistry*, 22: 2478–2486.

Cutting, et al. (1989) in Molecular Biological Methods for Bacillus. Harwood, C. R., and Cutting, S. M. (eds) John Wiley & Sons p.65

Higgins, D. G., and Sharp, P. M. (1988) Clustal: a package for performing multiple sequence alignment on microcomputer. Gene 73: 237–244

Ichikawa, Y., and Igarashi, Y. (1995) An extremely potent inhibitor for β-galactosidase. Tetrahedron Letters 36: 4585–4586

Kates, M., (1990) in Glycolipids, Phosphoglycolipids, and Sulfoglycolipids. Plenum Press p. 1–109

Laemmli, U. K. (1970) Cleavage of structural proteins during the assembly of the head of bacteriophage T4. Nature 227: 680–685

Linscheid, M., Diehl, B. W. K., Övermöhle, M., Riedl, I., and Heinz, E. (1997) Membrane lipids of Rhodopseudomonas viridis. Biochim. Biophys. Acta 1347:151–163

Roughan, P. G. and Beevers, H. (1981) Effects of cyanide on rates and products of fatty acid synthesis by chloroplasts isolated from Spinacia oleracea. Plant Physiol. 67: 926–929

Sambrook, J., Fritsch, E. F., and Maniatis, T. (1989) Molecular Cloning: A Laboratory Manual, 2nd edn. Cold spring Harbor Laboratory Press Shimojina, M., Ohta, Iwamatsu, A., Masuda, T., Shioi, Y., and Takamiya, K. (1997) Cloning of the gene for monogalactosyl diacylglycerol synthase and its evolutionary origin. Proc. Natl. Acad. Sci. 333–337

Vaccaro, A. M., Tatti, Ciaffoni, F., Salvioli, R., Barca, A., and Roncaioli, P. (1993) Studies on gluosylceramidase binding to phosphatidylserine liposomes: the role of bilayer curvature. Biochim Biophys Acta 1149(1):55–62

Vanderjagt, D. J., Fry, D. E., Glew R. H. (1994) Human glucocerebrosidase catalyses transglucosylation between glucocerebroside and retinol. Biochem J 300:309–15.

Yanish-Peron, C., Vieira, J., and Messing, J. (1985) Improved M13 phage cloning vectors and host strains: nucleotide sequence of the M13 mp 18 and pUC19 vectors. Gene 33: 103–119

What is claimed is:

1. A process for the production of a glucosyl diacylglycerol, a sterolglucoside, a glucocerebroside, an alkyl-β-D glucopyranoside, or a phosphoglucolipid in a cell by the use of a processive lipid glucosyl transferase that successively transfers a glucose residue to a lipid acceptor, comprising the steps of:
   transferring a nucleic acid molecule that codes for a protein having the enzymatic activity of a processive lipid glucosyl transferase to a cell, the protein having an amino acid sequence which is identical to the sequence selected from the sequences in the group consisting of SEQ ID NO:2 and SEQ ID NO:4; and
   expressing the protein having the enzymatic activity of a processive lipid glucosyl transferase under control of suitable regulatory sequences in the cell to produce a glucosyl diacylglycerol, a sterolglucoside, a glucocerebroside, an alkyl-β-D glucopyranoside, or a phosphoglucolipid.

2. The process according to claim 1, wherein the glucosyl diacylglycerol, the sterolglucoside, the glucocerebroside, the alkyl-β-D-glucopyranoside, or the phosphoglucolipid is selected from the group consisting of
   monoglucosyldiacyglycerol,
   diglucosyldiacylglycerol,
   triglucosyldiacylglycerol,
   tetraglucosyldiacylglycerol,
   glucosyl ceramide,
   diglucosyl ceramide,
   steryl glucoside,
   steryl diglucoside,
   glucosyl phosphatidylglycerol, and
   diglucosylphosphatidylglycerol.

3. The process according to claim 1, wherein the lipid acceptor is a secondary lipid acceptor, and wherein the secondary lipid acceptor is selected from the group consisting of a monohexosyldiacylglycerolipid, a dihexosyldiacylglycerolipid, a trihexosyldiacylgycerolipid, a tetrahexosyldiacylglycerolipid, a glycocerebroside, a dihexosylcerebroside, a sterolglycoside, a steroldiglycoside and a phosphoglycolipid.

4. The process according to claim 1, wherein the lipid acceptor is a primary lipid acceptor, and wherein the primary lipid acceptor is diacylglycerol, sterol, phosphatidylglycerol or ceramide.

5. The process according to claim 1, wherein the cell is selected from the group consisting of a plant cell, a yeast call, and a bacterial cell.

6. The process according to claim 1, further comprising recovering the glucosyl diacylglycerol, the sterolglucoside, the glucocerebroside, the alkyl-β-D-glucopyranoside, or the phosphoglucolipid synthesized by the enzymatic activity of the processive lipid glucosyl transferase from the cell.

* * * * *